(12) United States Patent
Daon et al.

(10) Patent No.: US 9,336,597 B2
(45) Date of Patent: May 10, 2016

(54) SYSTEM AND METHOD FOR DETERMINING THE THREE-DIMENSIONAL LOCATION AND ORIENATION OF IDENTIFICATION MARKERS

(71) Applicant: Navigate Surgical Technologies, Inc., Vancouver (CA)

(72) Inventors: Ehud (Udi) Daon, North Vancouver (CA); Martin Gregory Beckett, Bowen Island (CA)

(73) Assignee: Navigate Surgical Technologies, Inc., Vancouver (CA)

( * ) Notice: Subject to any disclaimer, the term of this patent is extended or adjusted under 35 U.S.C. 154(b) by 0 days.

(21) Appl. No.: 14/953,385

(22) Filed: Nov. 29, 2015

(65) Prior Publication Data

US 2016/0078627 A1 Mar. 17, 2016

Related U.S. Application Data

(63) Continuation-in-part of application No. 14/562,691, filed on Dec. 6, 2014, now Pat. No. 9,198,737, which is a continuation-in-part of application No. 13/713,165, filed on Dec. 13, 2012, now Pat. No. 8,908,918, and a continuation-in-part of application No. PCT/EP2013/073401, filed on Nov. 8, 2013.

(60) Provisional application No. 61/724,024, filed on Nov. 8, 2012.

(51) Int. Cl.
*G06K 9/00* (2006.01)
*G06T 7/00* (2006.01)
(Continued)

(52) U.S. Cl.
CPC ............... *G06T 7/0044* (2013.01); *A61B 6/14* (2013.01); *A61B 6/563* (2013.01); *G06K 9/3241* (2013.01); *G06T 7/0081* (2013.01); *G06T 7/20* (2013.01); *G06T 7/60* (2013.01); *A61B 2019/446* (2013.01); *A61B 2019/5265* (2013.01); *A61B 2019/5466* (2013.01); *A61B 2019/5483* (2013.01);
(Continued)

(58) Field of Classification Search
USPC ................. 382/103, 128, 209, 219, 278, 307; 128/922, 923
See application file for complete search history.

(56) References Cited

U.S. PATENT DOCUMENTS 6,414,746 B1 * 7/2002 Stettner ................. G01S 7/4816
250/332
7,653,455 B2 * 1/2010 Cinader, Jr. ............ A61C 1/084
433/24
(Continued)

*Primary Examiner* — Yosef Kassa
(74) *Attorney, Agent, or Firm* — Kevin R. Erdman; Brannon Sowers & Cracraft PC

(57) ABSTRACT

A three-dimensional position and orientation tracking system comprises one or more pattern tags, each comprising a plurality of contrasting portions, a tracker for obtaining image information about the pattern tags, a database with geometric information describing patterns on pattern tags; and a controller for receiving and processing the image information from the tracker, accessing the database to retrieve geometric information, and comparing the image information with the geometric information. The contrasting portions are arranged in a rotationally asymmetric pattern and at least one of the contrasting portions on a pattern tag comprising a perimeter with a polygonal shape. The pattern tags may be borne on tracking markers that have a three-dimensional shaped surface. The tracking system can be implemented in a surgical monitoring system in which the pattern tags are attached to tracking markers or are themselves tracking markers. A method associated with the system employs the rotationally asymmetric patterns on the tags to determine the three-dimensional locations and orientations of items bearing the tags using non-stereo image information.

31 Claims, 20 Drawing Sheets

(51) Int. Cl.
  *G06K 9/32* (2006.01)
  *G06T 7/20* (2006.01)
  *G06T 7/60* (2006.01)
  *A61B 6/14* (2006.01)
  *A61B 6/00* (2006.01)
  *A61B 19/00* (2006.01)

(52) U.S. Cl.
  CPC ..... *A61B2560/0475* (2013.01); *G06T 2200/04* (2013.01); *G06T 2207/30036* (2013.01); *G06T 2207/30052* (2013.01)

(56) References Cited

U.S. PATENT DOCUMENTS

| | | | | |
|---|---|---|---|---|
| 7,899,512 | B2 * | 3/2011 | Labadie | A61B 19/20 600/407 |
| 8,018,579 | B1 * | 9/2011 | Krah | G01B 11/00 356/4.01 |
| 8,395,482 | B2 * | 3/2013 | Sadr | G06K 7/10188 340/10.3 |
| 8,711,221 | B2 * | 4/2014 | Eggert | G06T 7/208 348/143 |

* cited by examiner

US 9,336,597 B2

SYSTEM AND METHOD FOR DETERMINING THE THREE-DIMENSIONAL LOCATION AND ORIENATION OF IDENTIFICATION MARKERS

CROSS REFERENCE TO RELATED APPLICATIONS

The present application is a continuation-in-part of U.S. patent application Ser. No. 14/562,691, filed Dec. 6, 2014, now U.S. Pat. No. 9,198,737, which is a continuation-in-part of PCT International Application Serial Number PCT/EP2013/073401, filed Nov. 8, 2013, and a continuation-in part of U.S. patent application Ser. No. 13/713,165, filed Dec. 13, 2012, now U.S. Pat. No. 8,908,918, both of which claim priority under 35 U.S.C. §119(e) of U.S. Patent Provisional Application Ser. No. 61/724,024, filed Nov. 8, 2012, the disclosures of which are incorporated by reference herein.

BACKGROUND OF THE INVENTION

1. Field of the Invention

The invention relates to location monitoring hardware and software systems. More specifically, the field of the invention is that of surgical equipment and software for monitoring surgical conditions.

2. Description of the Related Art

Visual and other sensory systems are known, with such systems being capable of both observing and monitoring surgical procedures. With such observation and monitoring systems, computer aided surgeries are now possible, and in fact are being routinely performed. In such procedures, the computer software interacts with both clinical images of the patient and observed surgical images from the current surgical procedure to provide guidance to the physician in conducting the surgery. For example, in one known system a carrier assembly bears at least one fiducial marker onto an attachment element in a precisely repeatable position with respect to a patient's jaw bone, employing the carrier assembly for providing registration between the fiducial marker and the patient's jaw bone and implanting the tooth implant by employing a tracking system which uses the registration to guide a drilling assembly. With this relatively new computer implemented technology, further improvements may further advance the effectiveness of surgical procedures.

SUMMARY OF THE INVENTION

The present invention is a surgical hardware and software monitoring system and method which allows for surgical planning while the patient is available for surgery, for example while the patient is being prepared for surgery so that the system may model the surgical site. In one embodiment, the model may be used to track contemplated surgical procedures and warn the physician regarding possible boundary violations that would indicate an inappropriate location in a surgical procedure. In another embodiment, the hardware may track the movement of instruments during the procedure and in reference to the model to enhance observation of the procedure. In this way, physicians are provided an additional tool to improve surgical planning and performance.

The system uses a particularly configured fiducial reference, to orient the monitoring system with regard to the critical area. The fiducial reference is attached to a location near the intended surgical area. For example, in the example of a dental surgery, a splint may be used to securely locate the fiducial reference near the surgical area. The fiducial reference may then be used as a point of reference, or a fiducial, for the further image processing of the surgical site. The fiducial reference may be identified relative to other portions of the surgical area by having a recognizable fiducial marker apparent in the scan.

The system of embodiments of the invention involves automatically computing the three-dimensional location of the patient by means of a tracking device that may be a tracking marker. The tracking marker may be attached in fixed spatial relation either directly to the fiducial reference, or attached to the fiducial reference via a tracking pole that itself may have a distinct three-dimensional shape. In the dental surgery example, a tracking pole is mechanically connected to the base of the fiducial reference that is in turn fixed in the patient's mouth. Each tracking pole device has a particular observation pattern, located either on itself or on a suitable tracking marker, and a particular geometrical connection to the base, which the computer software recognizes as corresponding to a particular geometry for subsequent location calculations. Although individual tracking pole devices have distinct configurations, they may all share the same connection base and thus may be used with any fiducial reference. The particular tracking information calculations are dictated by the particular tracking pole used, and actual patient location is calculated accordingly. Thus, tracking pole devices may be interchanged and calculation of the location remains the same. This provides, in the case of dental surgery, automatic recognition of the patient head location in space. Alternatively, a sensor device, or a tracker, may be in a known position relative to the fiducial key and its tracking pole, so that the current data image may be mapped to the scan image items.

The fiducial reference and each tracking pole or associated tracking marker may have a pattern made of radio opaque material so that when imaging information is scanned by the software, the particular items are recognized. Typically, each instrument used in the procedure has a unique pattern on its associated tracking marker so that the tracker information identifies the instrument. The software creates a model of the surgical site, in one embodiment a coordinate system, according to the location and orientation of the patterns on the fiducial reference and/or tracking pole(s) or their attached tracking markers. By way of example, in the embodiment where the fiducial reference has an associated pre-assigned pattern, analysis software interpreting image information from the tracker may recognize the pattern and may select the site of the base of the fiducial to be at the location where the fiducial reference is attached to a splint. If the fiducial key does not have an associated pattern, a fiducial site is designated. In the dental example this can be at a particular spatial relation to the tooth, and a splint location can be automatically designed for placement of the fiducial reference.

In a first aspect of the invention there is provided a surgical monitoring system comprising a fiducial reference configured for removably attaching to a location proximate a surgical site, for having a three-dimensional location and orientation determinable based on scan data of the surgical site, and for having the three-dimensional location and orientation determinable based on image information about the surgical site; a tracker arranged for obtaining the image information; and a controller configured for spatially relating the image information to the scan data and for determining the three-dimensional location and orientation of the fiducial reference. In one embodiment of the invention the fiducial reference may be rigidly and removably attachable to a part of the surgical site. In such an embodiment the fiducial reference may be repeatably attachable in the same three-dimensional orientation to the same location on the particular part of the surgical site.

The fiducial reference is at least one of marked and shaped for having at least one of its location and its orientation determined from the scan data and to allow it to be uniquely identified from the scan data. The surgical monitoring system further comprises a first tracking marker in fixed three-dimensional spatial relationship with the fiducial reference, wherein the first tracking marker is configured for having at least one of its location and its orientation determined by the controller based on the image information and the scan data. The first tracking marker may be configured to be removably and rigidly connected to the fiducial reference by a first tracking pole. The first tracking pole can have a three-dimensional structure uniquely identifiable by the controller from the image information. The three-dimensional structure of the first tracking pole allows its three-dimensional orientation of the first tracking pole to be determined by the controller from the image information.

The first tracking pole and fiducial reference may be configured to allow the first tracking pole to connect to a single unique location on the fiducial reference in a first single unique three-dimensional orientation. The fiducial reference may be configured for the attachment in a single second unique three-dimensional orientation of at least a second tracking pole attached to a second tracking marker. The first tracking marker may have a three-dimensional shape that is uniquely identifiable by the controller from the image information. The first tracking marker can have a three-dimensional shape that allows its three-dimensional orientation to be determined by the controller from the image information. The first tracking marker may have a marking that is uniquely identifiable by the controller and the marking may be configured for allowing at least one of its location and its orientation to be determined by the controller based on the image information and the scan data.

The surgical monitoring system may comprise further tracking markers attached to implements proximate the surgery site and the controller may be configured for determining locations and orientations of the implements based on the image information and information about the further tracking markers.

In another aspect of the invention there is provided a method for relating in real time the three-dimensional location and orientation of a surgical site on a patient to the location and orientation of the surgical site in a scan of the surgical site, the method comprising removably attaching a fiducial reference to a fiducial location on the patient proximate the surgical site; performing the scan with the fiducial reference attached to the fiducial location to obtain scan data; determining the three-dimensional location and orientation of the fiducial reference from the scan data; obtaining real time image information of the surgical site; determining in real time the three-dimensional location and orientation of the fiducial reference from the image information; deriving a spatial transformation matrix for expressing in real time the three-dimensional location and orientation of the fiducial reference as determined from the image information in terms of the three-dimensional location and orientation of the fiducial reference as determined from the scan data.

The obtaining of real time image information of the surgical site may comprise rigidly and removably attaching to the fiducial reference a first tracking marker in a fixed three-dimensional spatial relationship with the fiducial reference. The first tracking marker may be configured for having its location and its orientation determined based on the image information. The attaching of the first tracking marker to the fiducial reference may comprise rigidly and removably attaching the first tracking marker to the fiducial reference by means of a tracking pole. The obtaining of the real time image information of the surgical site may comprise rigidly and removably attaching to the fiducial reference a tracking pole in a fixed three-dimensional spatial relationship with the fiducial reference, and the tracking pole may have a distinctly identifiable three-dimensional shape that allows its location and orientation to be uniquely determined from the image information.

In yet a further aspect of the invention there is provided a method for real time monitoring the position of an object in relation to a surgical site of a patient, the method comprising removably attaching a fiducial reference to a fiducial location on the patient proximate the surgical site; performing a scan with the fiducial reference attached to the fiducial location to obtain scan data; determining the three-dimensional location and orientation of the fiducial reference from the scan data; obtaining real time image information of the surgical site; determining in real time the three-dimensional location and orientation of the fiducial reference from the image information; deriving a spatial transformation matrix for expressing in real time the three-dimensional location and orientation of the fiducial reference as determined from the image information in terms of the three-dimensional location and orientation of the fiducial reference as determined from the scan data; determining in real time the three-dimensional location and orientation of the object from the image information; and relating the three-dimensional location and orientation of the object to the three-dimensional location and orientation of the fiducial reference as determined from the image information. The determining in real time of the three-dimensional location and orientation of the object from the image information may comprise rigidly attaching a tracking marker to the object.

In one alternative embodiment, the tracker itself is attached to the fiducial reference so that the location of an object having a marker may be observed from a known position.

In another aspect there is presented a three-dimensional position and orientation tracking system comprising at least one pattern tag comprising a plurality of contrasting portions, a tracker configured for obtaining image information about the at least one pattern tag; a database comprising geometric information describing a pattern on the at least one pattern tag; and a controller configured for receiving and processing the image information from the tracker; accessing the database to retrieve geometric information; and comparing the image information with the geometric information; characterized in that the plurality of contrasting portions are arranged in a rotationally asymmetric pattern. The rotationally asymmetric pattern may be an identifiably unique pattern. The at least one of the plurality of contrasting portions may have a perimeter comprising a mathematically describable curved section. The perimeter of the at least one contrasting portion may comprise a conic section, including an ellipse or a circle. The at least one pattern tag may be flexible. The at least one pattern tag may be substantially planar. The at least one pattern tag may be a tracking marker. The tracking marker may have a surface that is a segment of a three-dimensional surface and the three-dimensional surface may be cylindrical or ellipsoid. The ellipsoid surface may be a spherical surface. In some embodiments, the plurality of contrasting portions may comprise a plurality of non-rectangularly confined contrasting portions arranged in a rotationally asymmetric pattern. In other embodiments the plurality of contrasting portions may comprise a plurality of unconfined contrasting portions arranged in a rotationally asymmetric pattern. In yet other embodiments, the plurality of contrasting portions may have a predetermined random distribution. The tracker may be a non-stereo tracker.

In another embodiment the three-dimensional position and orientation tracking system comprises at least two pattern tags, a first of the at least two pattern tags comprising a first plurality of contrasting portions and a second of the at least two pattern tags comprising at least one contrasting portion, a tracker configured for obtaining image information about the at least two pattern tags; a database comprising geometric information describing patterns on the at least two pattern tags; and a controller configured for receiving and processing the image information from the tracker; accessing the database to retrieve geometric information; and comparing the image information with the geometric information; characterized in that at least one of the first and second pattern tags has one or more contrasting portions arranged in a rotationally symmetric pattern; the contrasting portions of the first and second pattern tags together constitute a rotationally asymmetric pattern. The rotationally asymmetric pattern may be an identifiably unique pattern. The at least one contrasting portion of each of the at least two pattern tags may have a perimeter comprising a mathematically describable curved section. The perimeter of the at least one contrasting portion may comprise a conic section, including an ellipse or a circle. The pattern tags may be flexible and may be substantially planar. The at least two pattern tags together may constitute a tracking marker. The pattern tags may be afixed to tracking markers and the tracking markers may have a shape that comprises at least a portion having a three-dimensional surface and the three-dimensional surface may be cylindrical or ellipsoid. The ellipsoid surface may be a spherical surface.

In yet another aspect a method is provided for tracking an item bearing at least one pattern tag, the pattern tag bearing a rotationally asymmetric pattern having a plurality of contrasting portions, at least one of the plurality of contrasting portions having a perimeter comprising a mathematically describable curved section, the method comprising: obtaining from a tracker image information about the at least one pattern tag; obtaining from a database geometric information about the at least one pattern tag, the geometric information comprising a mathematical description of at least a section of the perimeter of the at least one contrasting portion of the at least one pattern tag; determining within the image information a three-dimensional location of at least one pattern reference point of the at least one pattern tag based on the geometric information, and determining within the image information a three-dimensional rotational orientation of the at least one pattern tag based on the geometric information. The plurality of contrasting portions may be a plurality of unconfined contrasting portions or non-rectangularly confined portions. In some embodiments of the method, the plurality of contrasting portions may have a predetermined random distribution; the geometric information may include predetermined distribution information about the random distribution; and the determining the three-dimensional location of the at least one pattern reference point may therefore comprise comparing the image information with the distribution information. The obtaining from a tracker image information may be obtaining from the tracker non-stereo image information.

In yet a further aspect there is provided a surgical monitoring system comprising a tracker for obtaining image information of a surgical site; a controller configured to spatially relate image information to previously obtained scan data; a fiducial reference configured for removably attaching to a location proximate the surgical site; a tracking marker in fixed three-dimensional spatial relationship with the fiducial reference and observable by the tracker, the tracking marker comprising a plurality of contrasting portions arranged in a rotationally asymmetric pattern; and controller software configured to allow the controller to determine the three-dimensional location and orientation of the fiducial reference based on the rotationally asymmetric pattern. The rotationally asymmetric pattern may be an identifiably unique pattern. The at least one of the contrasting portions may have a perimeter comprising a mathematically describable curved section and the controller software may be configured to allow the controller to determine at least one of the three-dimensional location and the orientation of the fiducial reference based on the mathematically describable curved section. The perimeter of the at least one contrasting portion may comprise a conic section, including an ellipse or a circle. The tracking marker may have a shape that comprises at least a portion having a three-dimensional surface and the three-dimensional surface may be cylindrical or ellipsoid. The ellipsoid surface may be a spherical surface. In some embodiments of the surgical monitoring system, the plurality of contrasting portions may comprise a plurality of non-rectangularly confined contrasting portions arranged in a rotationally asymmetric pattern. In other embodiments the plurality of contrasting portions may comprise a plurality of unconfined contrasting portions arranged in a rotationally asymmetric pattern. In yet other embodiments, the plurality of contrasting portions may have a predetermined random distribution. The tracker may be a non-stereo tracker.

In a further aspect a method is provided for tracking an item bearing a pattern tag having at least one unique rotationally asymmetric pattern, the method comprising: obtaining image information from a tracker about the at least one pattern tag; identifying the at least one pattern tag within the image information on the basis of its unique pattern; obtaining from a database geometric information about the at least one pattern tag, the geometric information comprising a mathematical description of at least a section of the perimeter of at least one contrasting portion of the at least one pattern tag; determining from the image information the location of at least one pattern reference point of the at least one pattern tag based on the geometric information; and determining from the image information the three-dimensional rotational orientation of the at least one pattern tag based on the geometric information and the at least one pattern reference point. The obtaining image information from the tracker may be obtaining non-stereo image information from the tracker.

In another embodiment, a method is provided for tracking the location and rotational orientation of an item comprising: attaching to the item a tracking marker bearing a rotationally asymmetric pattern of contrasting portions, at least a section of the perimeter of at least one contrasting portion of the at least one pattern tag having a mathematical description; obtaining image information from a tracker about the at least one pattern tag; obtaining geometric information from a database about the at least one pattern tag, the geometric information comprising a mathematical description of the at least a section of the perimeter of at the least one contrasting portion of the at least one pattern tag; determining from the image information the three-dimensional location of at least one pattern reference point of the at least one pattern tag based on the geometric information; and determining within the image information the three-dimensional rotational orientation of the at least one pattern tag based on the geometric information. The obtaining image information from a tracker may be obtaining non-stereo image information from the tracker. The plurality of contrasting portions may have a predetermined random distribution and the geometric information may include predetermined distribution information about the random distribution. In this embodiment of the method the determining the three-dimensional location of the at least one pattern reference point may comprise comparing the image information with the distribution information.

In some embodiments, the perimeters of the contrasting portions may be mathematically describable polygonal shapes instead of having mathematically describable curved sections.

BRIEF DESCRIPTION OF THE DRAWINGS

The above mentioned and other features and objects of this invention, and the manner of attaining them, will become more apparent and the invention itself will be better understood by reference to the following description of an embodiment of the invention taken in conjunction with the accompanying drawings, wherein.

Figure 1:
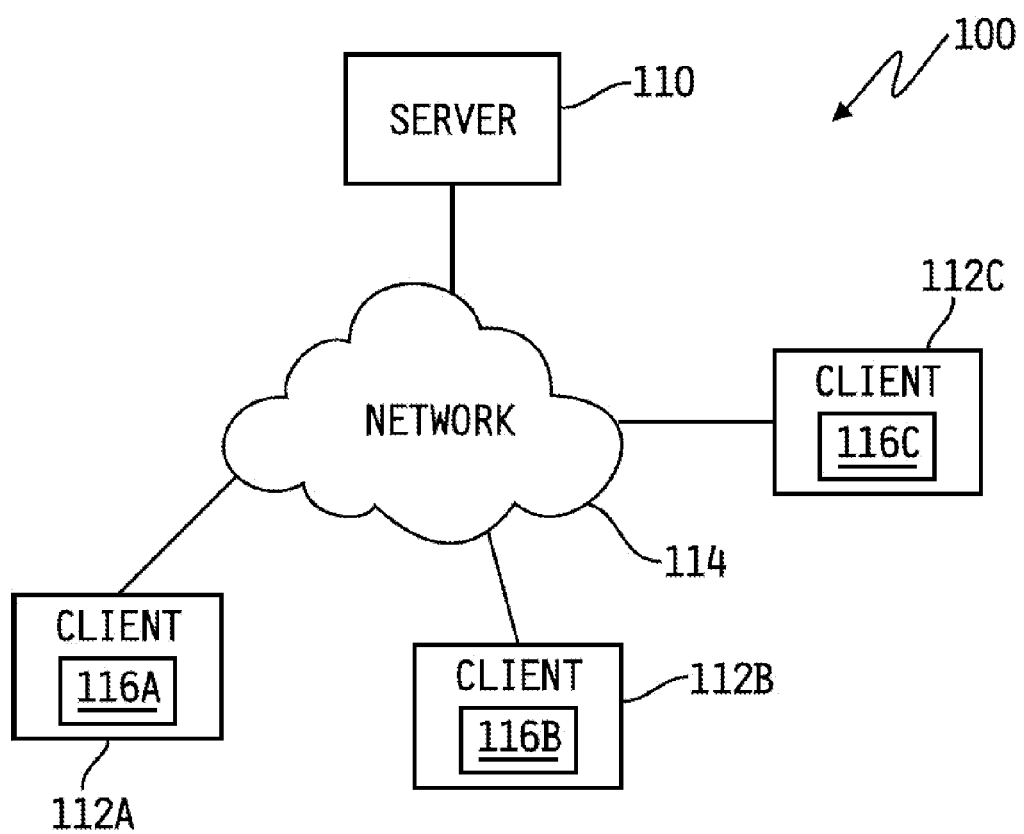
FIG. 1 is a schematic diagrammatic view of a network system in which embodiments of the present invention may be utilized.

Corresponding reference characters indicate corresponding parts throughout the several views. Although the drawings represent embodiments of the present invention, the drawings are not necessarily to scale and certain features may be exaggerated in order to better illustrate and explain the present invention. The flow charts and screen shots are also representative in nature, and actual embodiments of the invention may include further features or steps not shown in the drawings. The exemplification set out herein illustrates an embodiment of the invention, in one form, and such exemplifications are not to be construed as limiting the scope of the invention in any manner.

DESCRIPTION OF EMBODIMENTS OF THE PRESENT INVENTION

The embodiments disclosed below are not intended to be exhaustive or limit the invention to the precise form disclosed in the following detailed description. Rather, the embodiments are chosen and described so that others skilled in the art may utilize their teachings.

The detailed descriptions that follow are presented in part in terms of algorithms and symbolic representations of operations on data bits within a computer memory representing alphanumeric characters or other information. The hardware components are shown with particular shapes and relative orientations and sizes using particular scanning techniques, although in the general case one of ordinary skill recognizes that a variety of particular shapes and orientations and scanning methodologies may be used within the teaching of the present invention. A computer generally includes a processor for executing instructions and memory for storing instructions and data, including interfaces to obtain and process imaging data. When a general-purpose computer has a series of machine encoded instructions stored in its memory, the computer operating on such encoded instructions may become a specific type of machine, namely a computer particularly configured to perform the operations embodied by the series of instructions. Some of the instructions may be adapted to produce signals that control operation of other machines and thus may operate through those control signals to transform materials far removed from the computer itself. These descriptions and representations are the means used by those skilled in the art of data processing arts to most effectively convey the substance of their work to others skilled in the art.

An algorithm is here, and generally, conceived to be a self-consistent sequence of steps leading to a desired result. These steps are those requiring physical manipulations of physical quantities, observing and measuring scanned data representative of matter around the surgical site. Usually, though not necessarily, these quantities take the form of electrical or magnetic pulses or signals capable of being stored, transferred, transformed, combined, compared, and otherwise manipulated. It proves convenient at times, principally for reasons of common usage, to refer to these signals as bits, values, symbols, characters, display data, terms, numbers, or the like as a reference to the physical items or manifestations in which such signals are embodied or expressed to capture the underlying data of an image. It should be borne in mind, however, that all of these and similar terms are to be associated with the appropriate physical quantities and are merely used here as convenient labels applied to these quantities.

Some algorithms may use data structures for both inputting information and producing the desired result. Data structures greatly facilitate data management by data processing systems, and are not accessible except through sophisticated software systems. Data structures are not the information content of a memory, rather they represent specific electronic structural elements that impart or manifest a physical organization on the information stored in memory. More than mere abstraction, the data structures are specific electrical or magnetic structural elements in memory, which simultaneously represent complex data accurately, often data modeling physical characteristics of related items, and provide increased efficiency in computer operation.

Further, the manipulations performed are often referred to in terms, such as comparing or adding, commonly associated with mental operations performed by a human operator. No such capability of a human operator is necessary, or desirable in most cases, in any of the operations described herein that form part of the present invention; the operations are machine operations. Useful machines for performing the operations of the present invention include general-purpose digital computers or other similar devices. In all cases the distinction between the method operations in operating a computer and the method of computation itself should be recognized. The present invention relates to a method and apparatus for operating a computer in processing electrical or other (e.g., mechanical, chemical) physical signals to generate other desired physical manifestations or signals. The computer operates on software modules, which are collections of signals stored on a media that represents a series of machine instructions that enable the computer processor to perform the machine instructions that implement the algorithmic steps. Such machine instructions may be the actual computer code the processor interprets to implement the instructions, or alternatively may be a higher level coding of the instructions that is interpreted to obtain the actual computer code. The software module may also include a hardware component, wherein some aspects of the algorithm are performed by the circuitry itself rather as a result of an instruction.

The present invention also relates to an apparatus for performing these operations. This apparatus may be specifically constructed for the required purposes or it may comprise a general-purpose computer as selectively activated or reconfigured by a computer program stored in the computer. The algorithms presented herein are not inherently related to any particular computer or other apparatus unless explicitly indicated as requiring particular hardware. In some cases, the computer programs may communicate or relate to other programs or equipments through signals configured to particular protocols, which may or may not require specific hardware or programming to interact. In particular, various general-purpose machines may be used with programs written in accordance with the teachings herein, or it may prove more convenient to construct more specialized apparatus to perform the required method steps. The required structure for a variety of these machines will appear from the description below.

The present invention may deal with "object-oriented" software, and particularly with an "object-oriented" operating system. The "object-oriented" software is organized into "objects", each comprising a block of computer instructions describing various procedures ("methods") to be performed in response to "messages" sent to the object or "events" which occur with the object. Such operations include, for example, the manipulation of variables, the activation of an object by an external event, and the transmission of one or more messages to other objects. Often, but not necessarily, a physical object has a corresponding software object that may collect and transmit observed data from the physical device to the software system. Such observed data may be accessed from the physical object and/or the software object merely as an item of convenience; therefore where "actual data" is used in the following description, such "actual data" may be from the instrument itself or from the corresponding software object or module.

Messages are sent and received between objects having certain functions and knowledge to carry out processes. Messages are generated in response to user instructions, for example, by a user activating an icon with a "mouse" pointer generating an event. Also, messages may be generated by an object in response to the receipt of a message. When one of the objects receives a message, the object carries out an operation (a message procedure) corresponding to the message and, if necessary, returns a result of the operation. Each object has a region where internal states (instance variables) of the object itself are stored and where the other objects are not allowed to access. One feature of the object-oriented system is inheritance. For example, an object for drawing a "circle" on a display may inherit functions and knowledge from another object for drawing a "shape" on a display.

A programmer "programs" in an object-oriented programming language by writing individual blocks of code each of which creates an object by defining its methods. A collection of such objects adapted to communicate with one another by means of messages comprises an object-oriented program. Object-oriented computer programming facilitates the modeling of interactive systems in that each component of the system may be modeled with an object, the behavior of each component being simulated by the methods of its corresponding object, and the interactions between components being simulated by messages transmitted between objects.

An operator may stimulate a collection of interrelated objects comprising an object-oriented program by sending a message to one of the objects. The receipt of the message may cause the object to respond by carrying out predetermined functions, which may include sending additional messages to one or more other objects. The other objects may in turn carry out additional functions in response to the messages they receive, including sending still more messages. In this manner, sequences of message and response may continue indefinitely or may come to an end when all messages have been responded to and no new messages are being sent. When modeling systems utilizing an object-oriented language, a programmer need only think in terms of how each component of a modeled system responds to a stimulus and not in terms of the sequence of operations to be performed in response to some stimulus. Such sequence of operations naturally flows out of the interactions between the objects in response to the stimulus and need not be preordained by the programmer.

Although object-oriented programming makes simulation of systems of interrelated components more intuitive, the operation of an object-oriented program is often difficult to understand because the sequence of operations carried out by an object-oriented program is usually not immediately apparent from a software listing as in the case for sequentially organized programs Nor is it easy to determine how an object-oriented program works through observation of the readily apparent manifestations of its operation. Most of the operations carried out by a computer in response to a program are "invisible" to an observer since only a relatively few steps in a program typically produce an observable computer output.

In the following description, several terms that are used frequently have specialized meanings in the present context. The term "object" relates to a set of computer instructions and associated data, which may be activated directly or indirectly by the user. The terms "windowing environment", "running in windows", and "object oriented operating system" are used to denote a computer user interface in which information is manipulated and displayed on a video display such as within bounded regions on a raster scanned video display. The terms "network", "local area network", "LAN", "wide area network", or "WAN" mean two or more computers that are connected in such a manner that messages may be transmitted between the computers. In such computer networks, typically one or more computers operate as a "server", a computer with large storage devices such as hard disk drives and communication hardware to operate peripheral devices such as printers or modems. Other computers, termed "workstations", provide a user interface so that users of computer networks may access the network resources, such as shared data files, common peripheral devices, and inter-workstation communication. Users activate computer programs or network resources to create "processes" which include both the general operation of the computer program along with specific operating characteristics determined by input variables and its environment. Similar to a process is an agent (sometimes called an intelligent agent), which is a process that gathers information or performs some other service without user intervention and on some regular schedule. Typically, an agent, using parameters typically provided by the user, searches locations either on the host machine or at some other point on a network, gathers the information relevant to the purpose of the agent, and presents it to the user on a periodic basis.

The term "desktop" means a specific user interface which presents a menu or display of objects with associated settings for the user associated with the desktop. When the desktop accesses a network resource, which typically requires an application program to execute on the remote server, the desktop calls an Application Program Interface, or "API", to allow the user to provide commands to the network resource and observe any output. The term "Browser" refers to a program which is not necessarily apparent to the user, but which is responsible for transmitting messages between the desktop and the network server and for displaying and interacting with the network user. Browsers are designed to utilize a communications protocol for transmission of text and graphic information over a worldwide network of computers, namely the "World Wide Web" or simply the "Web". Examples of Browsers compatible with the present invention include the Internet Explorer program sold by Microsoft Corporation (Internet Explorer is a trademark of Microsoft Corporation), the Opera Browser program created by Opera Software ASA, or the Firefox browser program distributed by the Mozilla Foundation (Firefox is a registered trademark of the Mozilla Foundation). Although the following description details such operations in terms of a graphic user interface of a Browser, the present invention may be practiced with text based interfaces, or even with voice or visually activated interfaces, that have many of the functions of a graphic based Browser.

Browsers display information, which is formatted in a Standard Generalized Markup Language ("SGML") or a HyperText Markup Language ("HTML"), both being scripting languages, which embed non-visual codes in a text document through the use of special ASCII text codes. Files in these formats may be easily transmitted across computer networks, including global information networks like the Internet, and allow the Browsers to display text, images, and play audio and video recordings. The Web utilizes these data file formats to conjunction with its communication protocol to transmit such information between servers and workstations. Browsers may also be programmed to display information provided in an eXtensible Markup Language ("XML") file, with XML files being capable of use with several Document Type Definitions ("DTD") and thus more general in nature than SGML or HTML. The XML file may be analogized to an object, as the data and the stylesheet formatting are separately contained (formatting may be thought of as methods of displaying information, thus an XML file has data and an associated method).

The terms "personal digital assistant" or "PDA", as defined above, means any handheld, mobile device that combines computing, telephone, fax, e-mail and networking features. The terms "wireless wide area network" or "WWAN" mean a wireless network that serves as the medium for the transmission of data between a handheld device and a computer. The term "synchronization" means the exchanging of information between a first device, e.g. a handheld device, and a second device, e.g. a desktop computer, either via wires or wirelessly. Synchronization ensures that the data on both devices are identical (at least at the time of synchronization).

In wireless wide area networks, communication primarily occurs through the transmission of radio signals over analog, digital cellular, or personal communications service ("PCS") networks. Signals may also be transmitted through microwaves and other electromagnetic waves. At the present time, most wireless data communication takes place across cellular systems using second generation technology such as code-division multiple access ("CDMA"), time division multiple access ("TDMA"), the Global System for Mobile Communications ("GSM"), Third Generation (wideband or "3G"), Fourth Generation (broadband or "4G"), personal digital cellular ("PDC"), or through packet-data technology over analog systems such as cellular digital packet data (CDPD") used on the Advance Mobile Phone Service ("AMPS").

The terms "wireless application protocol" or "WAP" mean a universal specification to facilitate the delivery and presentation of web-based data on handheld and mobile devices with small user interfaces. "Mobile Software" refers to the software operating system, which allows for application programs to be implemented on a mobile device such as a mobile telephone or PDA. Examples of Mobile Software are Java and Java ME (Java and JavaME are trademarks of Sun Microsystems, Inc. of Santa Clara, Calif.), BREW (BREW is a registered trademark of Qualcomm Incorporated of San Diego, Calif.), Windows Mobile (Windows is a registered trademark of Microsoft Corporation of Redmond, Wash.), Palm OS (Palm is a registered trademark of Palm, Inc. of Sunnyvale, Calif.), Symbian OS (Symbian is a registered trademark of Symbian Software Limited Corporation of London, United Kingdom), ANDROID OS (ANDROID is a registered trademark of Google, Inc. of Mountain View, Calif.), and iPhone OS (iPhone is a registered trademark of Apple, Inc. of Cupertino, Calif.), and Windows Phone 7. "Mobile Apps" refers to software programs written for execution with Mobile Software.

The terms "scan," "fiducial reference", "fiducial location", "marker," "tracker" and "image information" have particular meanings in the present disclosure. For purposes of the present disclosure, "scan" or derivatives thereof refer to x-ray, magnetic resonance imaging (MRI), computerized tomography (CT), sonography, cone beam computerized tomography (CBCT), or any system that produces a quantitative spatial representation of a patient. The term "fiducial reference" or simply "fiducial" refers to an object or reference on the image of a scan that is uniquely identifiable as a fixed recognizable point. In the present specification the term "fiducial location" refers to a useful location to which a fiducial reference is attached. A "fiducial location" will typically be proximate a surgical site. The term "marker" or "tracking marker" refers to an object or reference that may be perceived by a sensor proximate to the location of the surgical or dental procedure, where the sensor may be an optical sensor, a radio frequency identifier (RFID), a sonic motion detector, an ultra-violet or infrared sensor. The term "tracker" refers to a device or system of devices able to determine the location of the markers and their orientation and movement continually in 'real time' during a procedure. As an example of a possible implementation, if the markers are composed of printed targets then the tracker may include a stereo camera pair. The term "image information" is used in the present specification to describe information obtained by the tracker, whether optical or otherwise, and usable for determining the location of the markers and their orientation and movement continually in 'real time' during a procedure.

FIG. 1 is a high-level block diagram of a computing environment 100 according to one embodiment. FIG. 1 illustrates server 110 and three clients 112 connected by network 114. Only three clients 112 are shown in FIG. 1 in order to simplify and clarify the description. Embodiments of the computing environment 100 may have thousands or millions of clients 112 connected to network 114, for example the Internet. Users (not shown) may operate software 116 on one of clients 112 to both send and receive messages network 114 via server 110 and its associated communications equipment and software (not shown).

Figure 2:
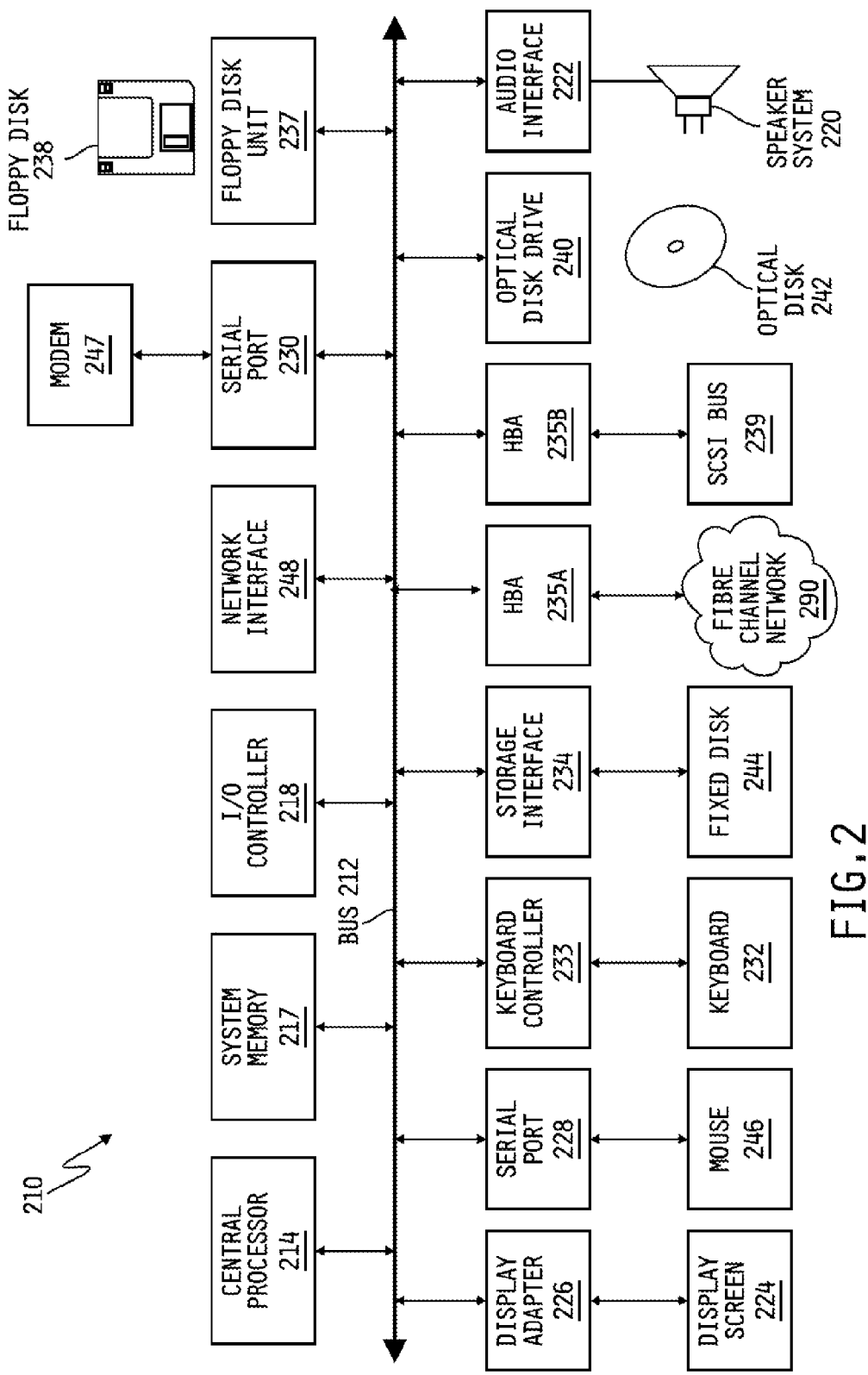
FIG. 2 is a block diagram of a computing system (either a server or client, or both, as appropriate), with optional input devices (e.g., keyboard, mouse, touch screen, etc.) and output devices, hardware, network connections, one or more processors, and memory/storage for data and modules, etc. which may be utilized as controller and display in conjunction with embodiments of the present invention.

FIG. 2 depicts a block diagram of computer system 210 suitable for implementing server 110 or client 112. Computer system 210 includes bus 212 which interconnects major subsystems of computer system 210, such as central processor 214, system memory 217 (typically RAM, but which may also include ROM, flash RAM, or the like), input/output controller 218, external audio device, such as speaker system 220 via audio output interface 222, external device, such as display screen 224 via display adapter 226, serial ports 228 and 230, keyboard 232 (interfaced with keyboard controller 233), storage interface 234, disk drive 237 operative to receive floppy disk 238, host bus adapter (HBA) interface card 235A operative to connect with Fibre Channel network 290, host bus adapter (HBA) interface card 235B operative to connect to SCSI bus 239, and optical disk drive 240 operative to receive optical disk 242. Also included are mouse 246 (or other point-and-click device, coupled to bus 212 via serial port 228), modem 247 (coupled to bus 212 via serial port 230), and network interface 248 (coupled directly to bus 212).

Bus 212 allows data communication between central processor 214 and system memory 217, which may include read-only memory (ROM) or flash memory (neither shown), and random access memory (RAM) (not shown), as previously noted. RAM is generally the main memory into which operating system and application programs are loaded. ROM or flash memory may contain, among other software code, Basic Input-Output system (BIOS), which controls basic hardware operation such as interaction with peripheral components. Applications resident with computer system 210 are generally stored on and accessed via computer readable media, such as hard disk drives (e.g., fixed disk 244), optical drives (e.g., optical drive 240), floppy disk unit 237, or other storage medium. Additionally, applications may be in the form of electronic signals modulated in accordance with the application and data communication technology when accessed via network modem 247 or interface 248 or other telecommunications equipment (not shown).

Storage interface 234, as with other storage interfaces of computer system 210, may connect to standard computer readable media for storage and/or retrieval of information, such as fixed disk drive 244. Fixed disk drive 244 may be part of computer system 210 or may be separate and accessed through other interface systems. Modem 247 may provide direct connection to remote servers via telephone link or the Internet via an Internet service provider (ISP) (not shown). Network interface 248 may provide direct connection to remote servers via direct network link to the Internet via a POP (point of presence). Network interface 248 may provide such connection using wireless techniques, including digital cellular telephone connection, Cellular Digital Packet Data (CDPD) connection, digital satellite data connection or the like.

Many other devices or subsystems (not shown) may be connected in a similar manner (e.g., document scanners, digital cameras and so on), including the hardware components of FIGS. 3A-I, which alternatively may be in communication with associated computational resources through local, wide-area, or wireless networks or communications systems. Thus, while the disclosure may generally discuss an embodiment where the hardware components are directly connected to computing resources, one of ordinary skill in this area recognizes that such hardware may be remotely connected with computing resources. Conversely, all of the devices shown in FIG. 2 need not be present to practice the present disclosure. Devices and subsystems may be interconnected in different ways from that shown in FIG. 2. Operation of a computer system such as that shown in FIG. 2 is readily known in the art and is not discussed in detail in this application. Software source and/or object codes to implement the present disclosure may be stored in computer-readable storage media such as one or more of system memory 217, fixed disk 244, optical disk 242, or floppy disk 238. The operating system provided on computer system 210 may be a variety or version of either MS-DOS® (MS-DOS is a registered trademark of Microsoft Corporation of Redmond, Wash.), WINDOWS® (WINDOWS is a registered trademark of Microsoft Corporation of Redmond, Wash.), OS/2® (OS/2 is a registered trademark of International Business Machines Corporation of Armonk, N.Y.), UNIX® (UNIX is a registered trademark of X/Open Company Limited of Reading, United Kingdom), Linux® (Linux is a registered trademark of Linus Torvalds of Portland, Oreg.), or other known or developed operating system.

Moreover, regarding the signals described herein, those skilled in the art recognize that a signal may be directly transmitted from a first block to a second block, or a signal may be modified (e.g., amplified, attenuated, delayed, latched, buffered, inverted, filtered, or otherwise modified) between blocks. Although the signals of the above-described embodiments are characterized as transmitted from one block to the next, other embodiments of the present disclosure may include modified signals in place of such directly transmitted signals as long as the informational and/or functional aspect of the signal is transmitted between blocks. To some extent, a signal input at a second block may be conceptualized as a second signal derived from a first signal output from a first block due to physical limitations of the circuitry involved (e.g., there will inevitably be some attenuation and delay). Therefore, as used herein, a second signal derived from a first signal includes the first signal or any modifications to the first signal, whether due to circuit limitations or due to passage through other circuit elements which do not change the informational and/or final functional aspect of the first signal.

The present invention relates to a surgical hardware and software monitoring system and method which allows for surgical planning while the patient is available for surgery, for example while the patient is being prepared for surgery so that the system may model the surgical site. The system uses a particularly configured piece of hardware, represented as fiducial key 10 in FIG. 3A, to orient tracking marker 12 of the monitoring system with regard to the critical area of the surgery. Fiducial key 10 is attached to a location near the intended surgical area, in the exemplary embodiment of the dental surgical area of FIG. 3A, fiducial key 10 is attached to a dental splint 14. Tracking marker 12 may be connected to fiducial key 10 by tracking pole 11. In embodiments in which the fiducial reference is directly visible to a suitable tracker (see for example FIG. 5 and FIG. 6) that acquires image information about the surgical site, a tracking marker may be attached directly to the fiducial reference. For example a dental surgery, the dental tracking marker 14 may be used to securely locate the fiducial 10 near the surgical area. The fiducial key 10 may be used as a point of reference, or a fiducial, for the further image processing of data acquired from tracking marker 12 by the tracker.

In other embodiments additional tracking markers 12 may be attached to items independent of the fiducial key 10 and any of its associated tracking poles 11 or tracking markers 12. This allows the independent items to be tracked by the tracker.

In a further embodiment at least one of the items or instruments near the surgical site may optionally have a tracker attached to function as tracker for the monitoring system of the invention and to thereby sense the orientation and the position of the tracking marker 12 and of any other additional tracking markers relative to the scan data of the surgical area. By way of example, the tracker attached to an instrument may be a miniature digital camera and it may be attached, for example, to a dentist's drill. Any other markers to be tracked by the tracker attached to the item or instrument must be within the field of view of the tracker.

Using the dental surgery example, the patient is scanned to obtain an initial scan of the surgical site. The particular configuration of fiducial key 10 allows computer software stored in memory and executed in a suitable controller, for example processor 214 and memory 217 of computer 210 of FIG. 2, to recognize its relative position within the surgical site from the scan data, so that further observations may be made with reference to both the location and orientation of fiducial key 10. In some embodiments, the fiducial reference includes a marking that is apparent as a recognizable identifying symbol when scanned. In other embodiments, the fiducial reference includes a shape that is distinct in the sense that the body apparent on the scan has an asymmetrical form allowing the front, rear, upper, and lower, and left/right defined surfaces that may be unambiguously determined from the analysis of the scan, thereby to allow the determination not only of the location of the fiducial reference, but also of its orientation.

In addition, the computer software may create a coordinate system for organizing objects in the scan, such as teeth, jaw bone, skin and gum tissue, other surgical instruments, etc. The coordinate system relates the images on the scan to the space around the fiducial and locates the instruments bearing tracking markers both by orientation and position. The model generated by the monitoring system may then be used to check boundary conditions, and in conjunction with the tracker display the arrangement in real time on a suitable display, for example display 224 of FIG. 2.

In one embodiment, the computer system has a predetermined knowledge of the physical configuration of fiducial key 10 and examines slices/sections of the scan to locate fiducial key 10. Locating of fiducial key 10 may be on the basis of its distinct shape, or on the basis of distinctive identifying and orienting markings upon the fiducial key or on attachments to the fiducial key 10 as tracking marker 12. Fiducial key 10 may be rendered distinctly visible in the scans through higher imaging contrast by the employ of radio-opaque materials or high-density materials in the construction of the fiducial key 10. In other embodiments the material of the distinctive identifying and orienting markings may be created using suitable high density or radio-opaque inks or materials.

Once fiducial key 10 is identified, the location and orientation of the fiducial key 10 is determined from the scan segments, and a point within fiducial key 10 is assigned as the center of the coordinate system. The point so chosen may be chosen arbitrarily, or the choice may be based on some useful criterion. A model is then derived in the form of a transformation matrix to relate the fiducial system, being fiducial key 10 in one particular embodiment, to the coordinate system of the surgical site. The resulting virtual construct may be used by surgical procedure planning software for virtual modeling of the contemplated procedure, and may alternatively be used by instrumentation software for the configuration of the instrument, for providing imaging assistance for surgical software, and/or for plotting trajectories for the conduct of the surgical procedure.

Figure 3A:
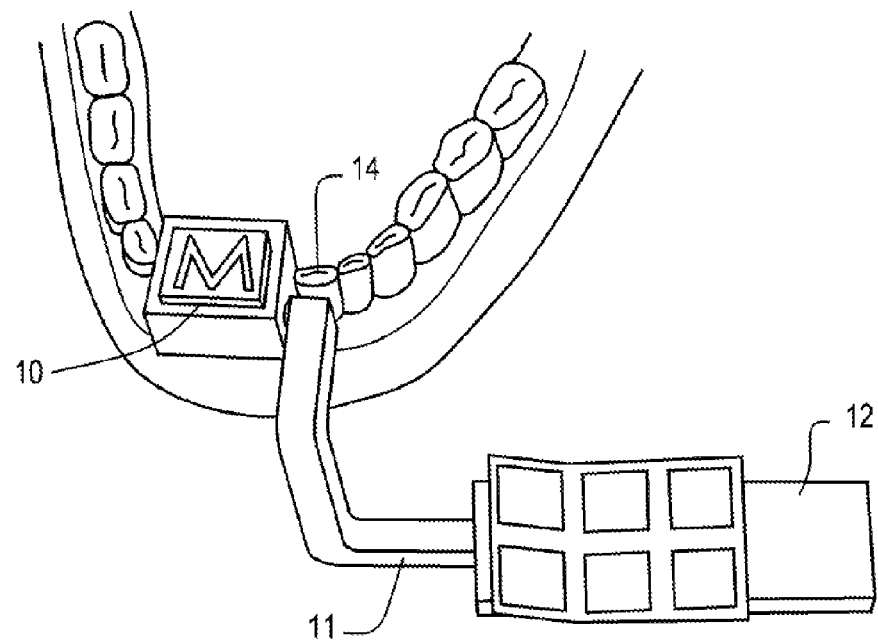
FIGS. 3A-L are drawings of hardware components of the surgical monitoring system according to embodiments of the invention.
Figure 3B:
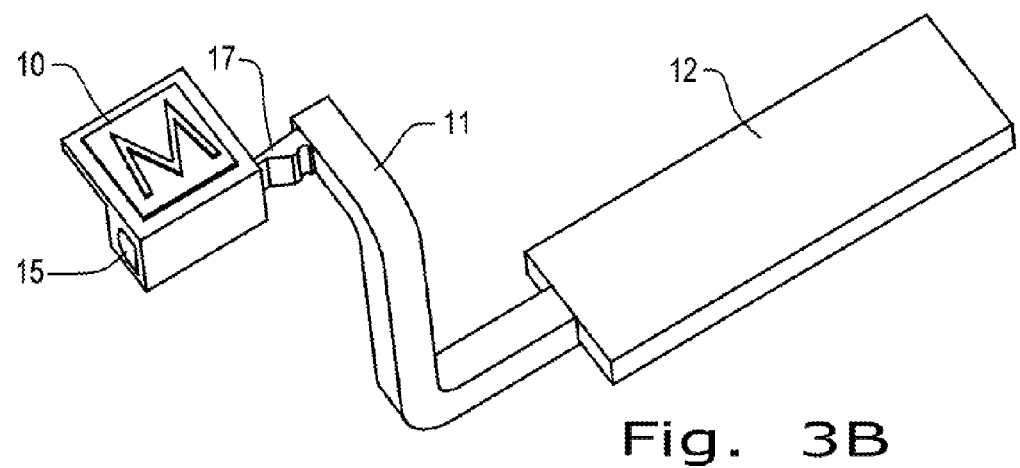
Figure 3C:
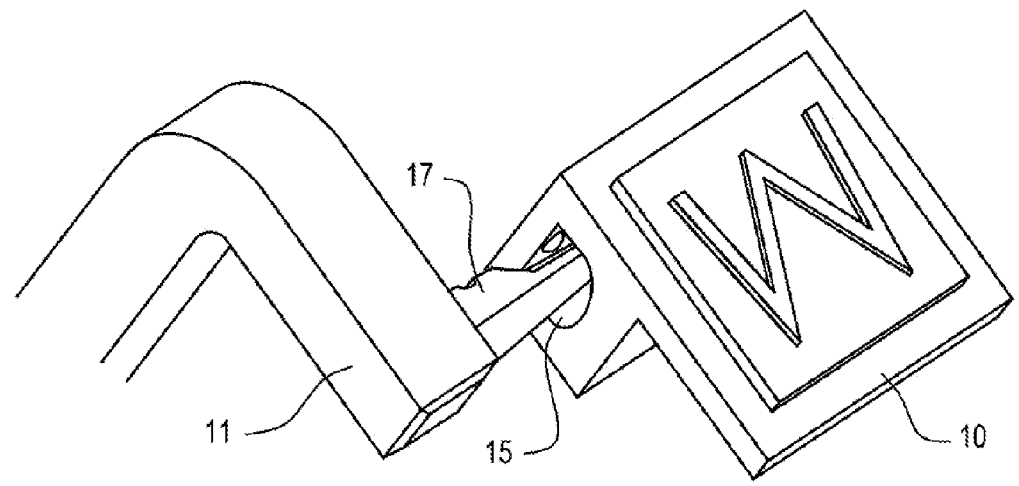
Figure 3D:
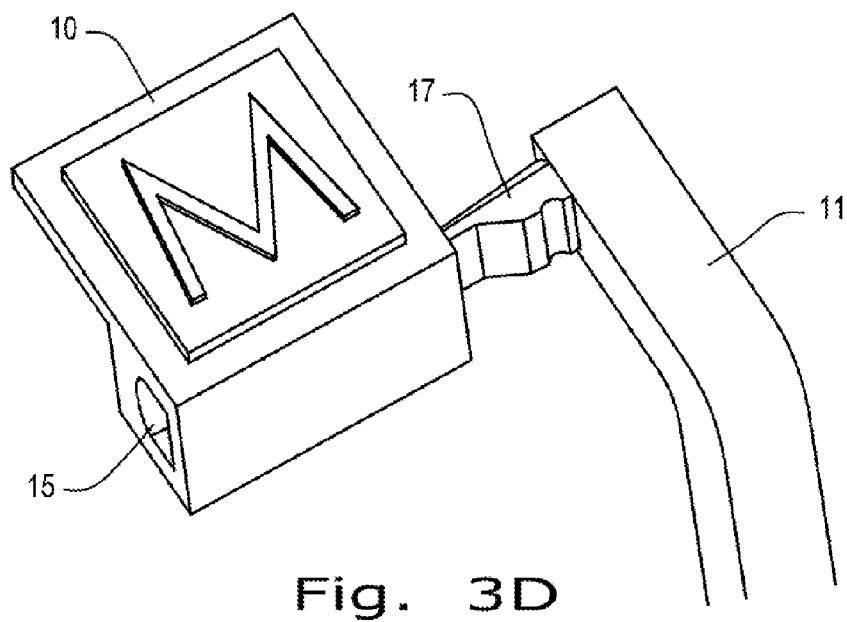
Figure 3E:
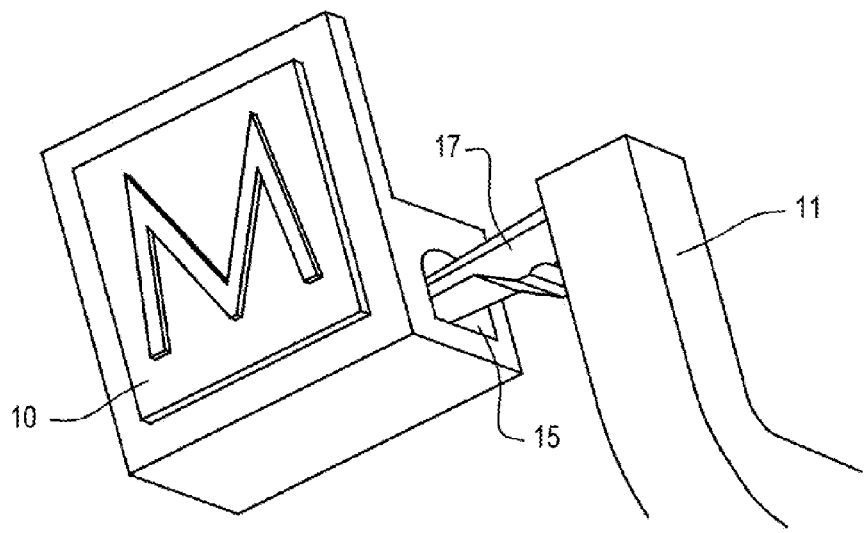
Figure 3F:
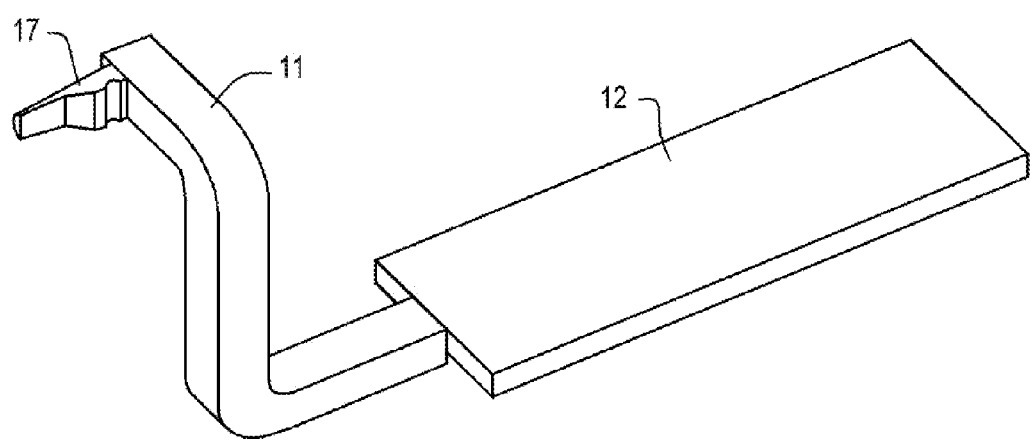

In some embodiments, the monitoring hardware includes a tracking attachment to the fiducial reference. In the embodiment pertaining to dental surgery the tracking attachment to fiducial key 10 is tracking marker 12, which is attached to fiducial key 10 via tracking pole 11. Tracking marker 12 may have a particular identifying pattern. The trackable attachment, for example tracking marker 12, and even associated tracking pole 11 may have known configurations so that observational data from tracking pole 11 and/or tracking marker 12 may be precisely mapped to the coordinate system, and thus progress of the surgical procedure may be monitored and recorded. For example, as particularly shown in FIG. 3J, fiducial key 10 may have hole 15 in a predetermined location specially adapted for engagement with insert 17 of tracking pole 11. In such an arrangement, for example, tracking poles 11 may be attached with a low force push into hole 15 of fiducial key 10, and an audible haptic notification may thus be given upon successful completion of the attachment.

It is further possible to reorient the tracking pole during a surgical procedure. Such reorientation may be in order to change the location of the procedure, for example where a dental surgery deals with teeth on the opposite side of the mouth, where a surgeon switches hands, and/or where a second surgeon performs a portion of the procedure. For example, the movement of the tracking pole may trigger a re-registration of the tracking pole with relation to the coordinate system, so that the locations may be accordingly adjusted. Such a re-registration may be automatically initiated when, for example in the case of the dental surgery embodiment, tracking pole 11 with its attached tracking marker 12 are removed from hole 15 of fiducial key 10 and another tracking marker with its associated tracking pole is connected to an alternative hole on fiducial key 10. Additionally, boundary conditions may be implemented in the software so that the user is notified when observational data approaches and/or enters the boundary areas.

In a further embodiment, the tracking markers may specifically have a three dimensional shape. Suitable three-dimensional shapes bearing identifying patterns may include, without limitation, a segment of an ellipsoid surface and a segment of a cylindrical surface. In general, suitable three-dimensional shapes are shapes that are mathematically describable by simple functions. One particular three-dimensional surface suitable for use as tracking marker 312 in this embodiment is a cylindrical surface, as shown in FIG. 3K. A cylindrical surface is mathematically described by a simple function. Pattern 313 is rotationally asymmetric, so that rotating cylindrically shaped tracking marker 312 never causes pattern 313 to repeat itself spatially. This allows the position and orientation of tracking marker 312 to be uniquely determined. Pattern 313 may be present over any useful segment of the surface of tracking marker 312, and may extend around the full circular perimeter of tracking marker 312, thereby allowing a suitable tracker (not shown) to always have a portion of pattern 313 in its view, irrespective of the orientation of position of tracking marker 312. Tracking marker 312 may engage with tracking pole 11 in exactly the same way as already described in the case of tracking markers 12. In FIG. 3K, tracking marker 312 is shown as comprising of five rings of patterns which, together, comprise pattern 313. In other embodiments tracking marker 312 may comprise a single ring bearing a suitably rotationally asymmetric pattern 313 and tracking marker 312 may thereby be a simple ring bearing pattern 313.

Further embodiments of suitable tracking markers bearing rotationally asymmetric patterns are described later at the hand of FIGS. 7-10. The contrast aspects discussed below at the hand of FIGS. 7-10 also apply to pattern 313 in FIG. 3K in that the contrasting portions of pattern 313 may have perimeters comprising a mathematically describable curved sections to provide suitable pattern tags. More detail in this regard is provided below.

In another embodiment, a suitable segment of a three-dimensional surface for use as a pattern bearing surface for a tracking marker is an ellipsoid surface. Ellipsoids are describable by simple mathematical functions, of which a spherical surface is the most simple and the surface extends in three dimensions (i.e. not flat and extending in only two dimensions). FIG. 3L shows tracking marker 322 having an ellipsoid surface bearing a pattern 323. Tracking marker 322 may be used in the same fashion as tracking marker 312, or the tracking markers of FIGS. 7-10, 15, 16, 17, and 18.

In both FIG. 3K and FIG. 3L patterns 313 and 323 respectively are shown as black circular areas on a white background. In other embodiments, the circular contrast areas may be white and the background color may be black. In yet further embodiments, other mutually contrasting colors, tones, or hues may be employed in the visible or infrared spectrum for the circular contrast areas and for the background, as described later below at the hand of FIG. 7.

The tracker of the system may comprise a single imager obtaining a two-dimensional image of the site being monitored. The system and method described in the present specification allow three-dimensional locations and orientations of tracking markers to be obtained using non-stereo-pair two-dimensional imagery. In some embodiments more than one imager may be employed as tracker, but the image information required and employed is nevertheless two-dimensional. Therefore the two imagers may merely be employed to secure different perspective views of the site, each imager rendering a two-dimensional image that is not part of a stereo pair. This does not exclude the employment of stereo-imagers in obtaining the image information about the site, but the system and method are not reliant on stereo imagery of the site.

In a further embodiment of the system utilizing the invention, a surgical instrument or implement, herein termed a "hand piece" (see FIGS. 5 and 6), may also have a particular configuration that may be located and tracked in the coordinate system and may have suitable tracking markers as described herein. A boundary condition may be set up to indicate a potential collision with virtual material, so that when the hand piece is sensed to approach the boundary condition an indication may appear on a screen, or an alarm sound. Further, target boundary conditions may be set up to indicate the desired surgical area, so that when the trajectory of the hand piece is trending outside the target area an indication may appear on screen or an alarm sound indicating that the hand piece is deviating from its desired path.

Figure 3G:
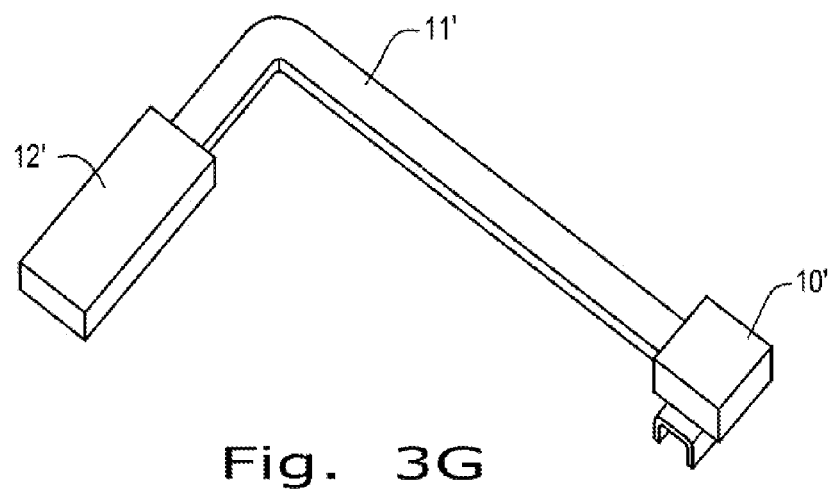
Figure 3H:
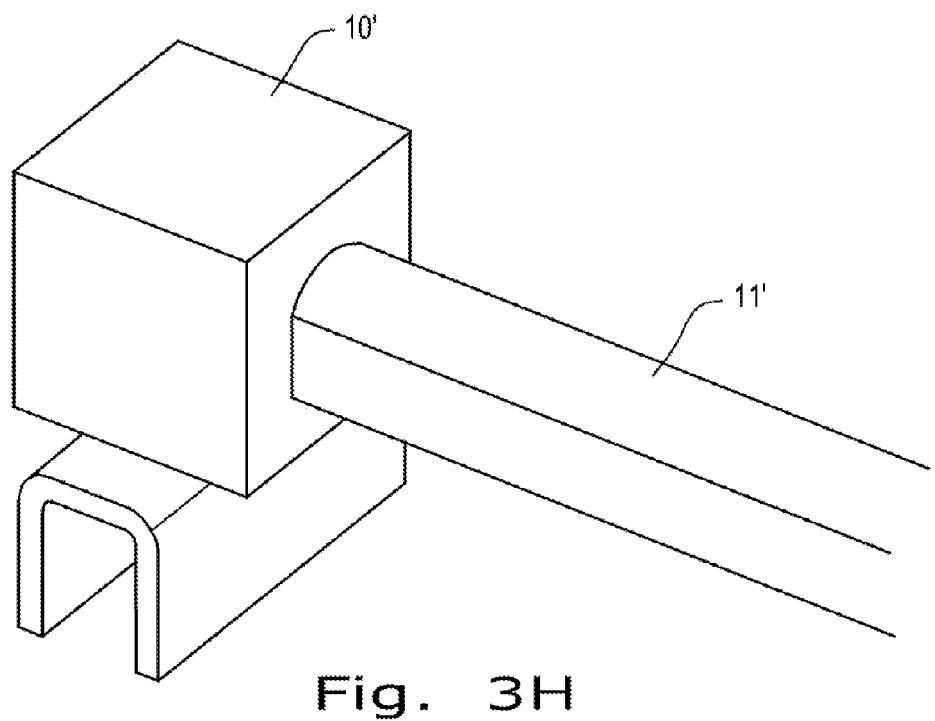
Figure 3I:
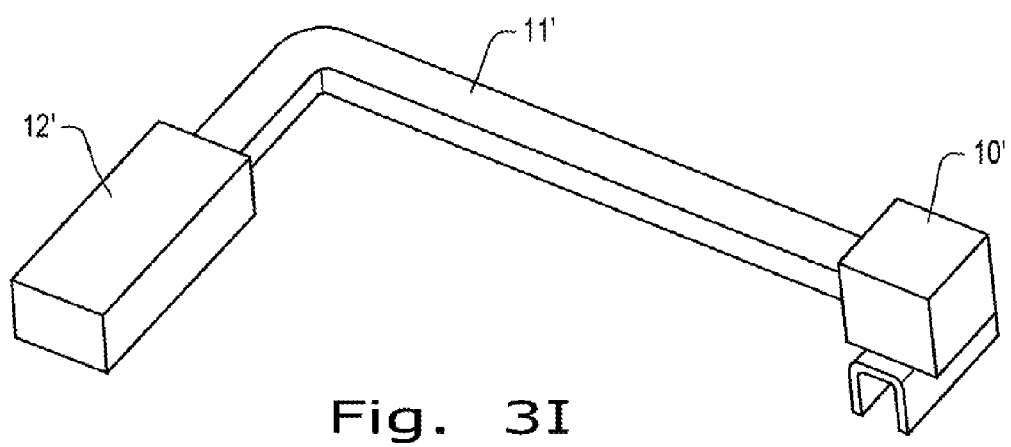
Figure 3J:
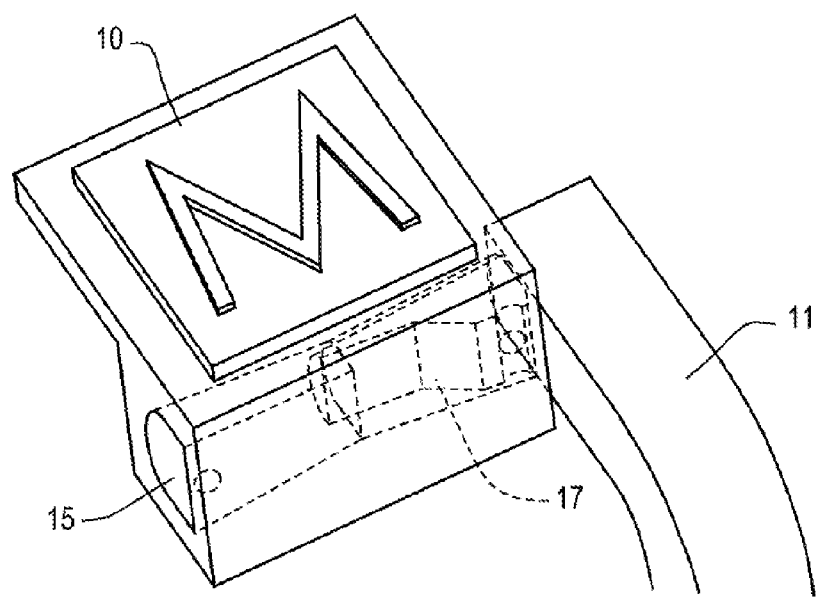
Figure 3K:
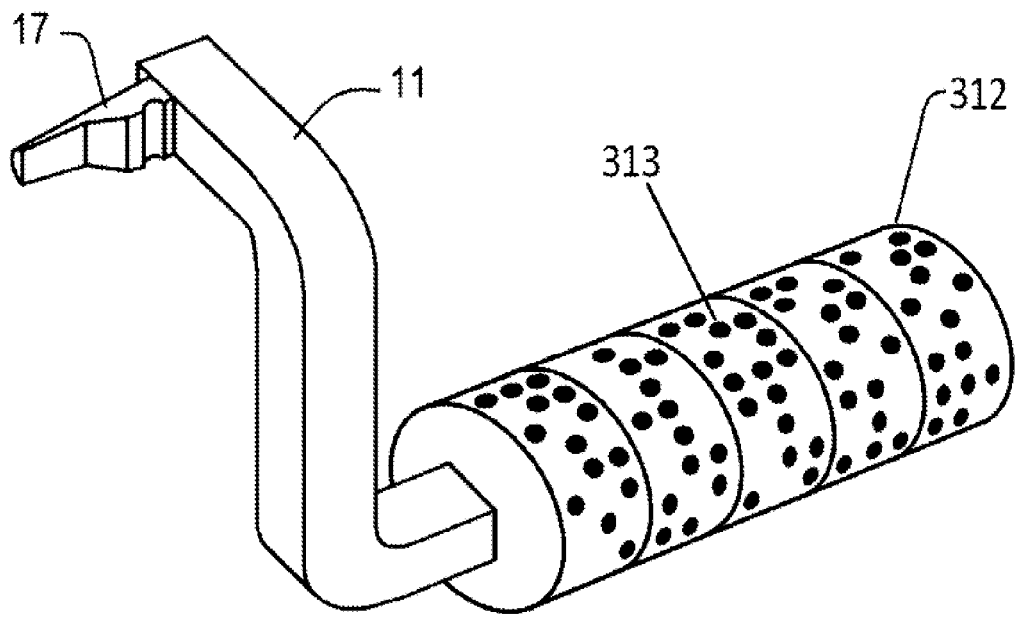
Figure 3L:
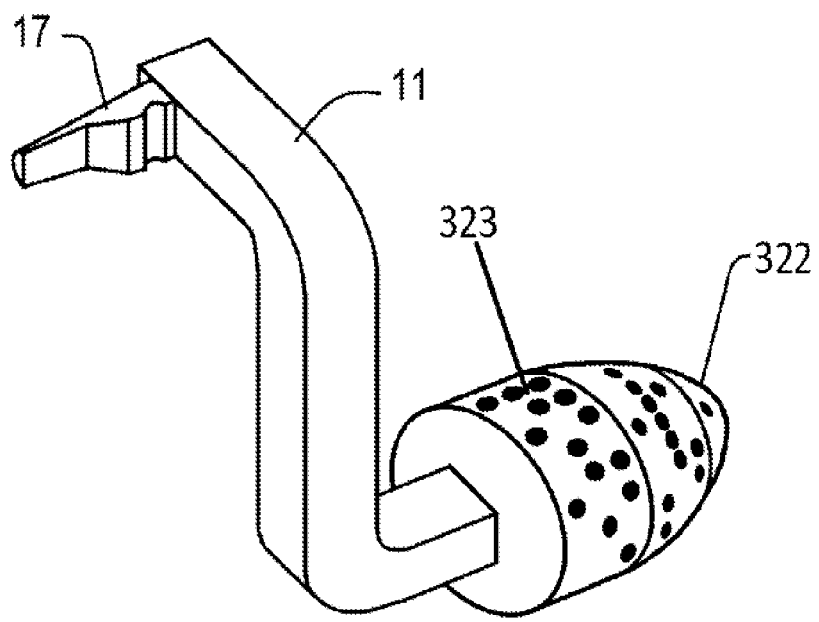

An alternative embodiment of some hardware components are shown in FIGS. 3G-I. Fiducial key 10' has connection elements with suitable connecting portions to allow a tracking pole 11' to position a tracking marker 12' relative to the surgical site. Conceptually, fiducial key 10' serves as an anchor for pole 11' and tracking marker 12' in much the same way as the earlier embodiment, although it has a distinct shape. The software of the monitoring system is pre-programmed with the configuration of each particularly identified fiducial key, tracking pole, and tracking marker, so that the location calculations are only changed according to the changed configuration parameters.

The materials of the hardware components may vary according to regulatory requirements and practical considerations. Generally, the key or fiducial component is made of generally radio opaque material such that it does not produce noise for the scan, yet creates recognizable contrast on the scanned image so that any identifying pattern associated with it may be recognized. In addition, because it is generally located on the patient, the material should be lightweight and suitable for connection to an apparatus on the patient. For example, in the dental surgery example, the materials of the fiducial key must be suitable for connection to a plastic splint and suitable for connection to a tracking pole. In the surgical example the materials of the fiducial key may be suitable for attachment to the skin or other particular tissue of a patient.

The tracking markers are clearly identified by employing, for example without limitation, high contrast pattern engraving. The materials of the tracking markers are chosen to be capable of resisting damage in autoclave processes and are compatible with rigid, repeatable, and quick connection to a connector structure. The tracking markers and associated tracking poles have the ability to be accommodated at different locations for different surgery locations, and, like the fiducial keys, they should also be relatively lightweight as they will often be resting on or against the patient. The tracking poles must similarly be compatible with autoclave processes and have connectors of a form shared among tracking poles.

The tracker employed in tracking the fiducial keys, tracking poles and tracking markers should be capable of tracking with suitable accuracy objects of a size of the order of 1.5 square centimeters. The tracker may be, by way of example without limitation, a stereo camera or stereo camera pair. While the tracker is generally connected by wire to a computing device to read the sensory input, it may optionally have wireless connectivity to transmit the sensory data to a computing device.

In embodiments that additionally employ a trackable piece of instrumentation, such as a hand piece, tracking markers attached to such a trackable piece of instrumentation may also be light-weight; capable of operating in a 3-object array with 90 degrees relationship; optionally having a high contrast pattern engraving and a rigid, quick mounting mechanism to a standard hand piece.

Figure 4A:
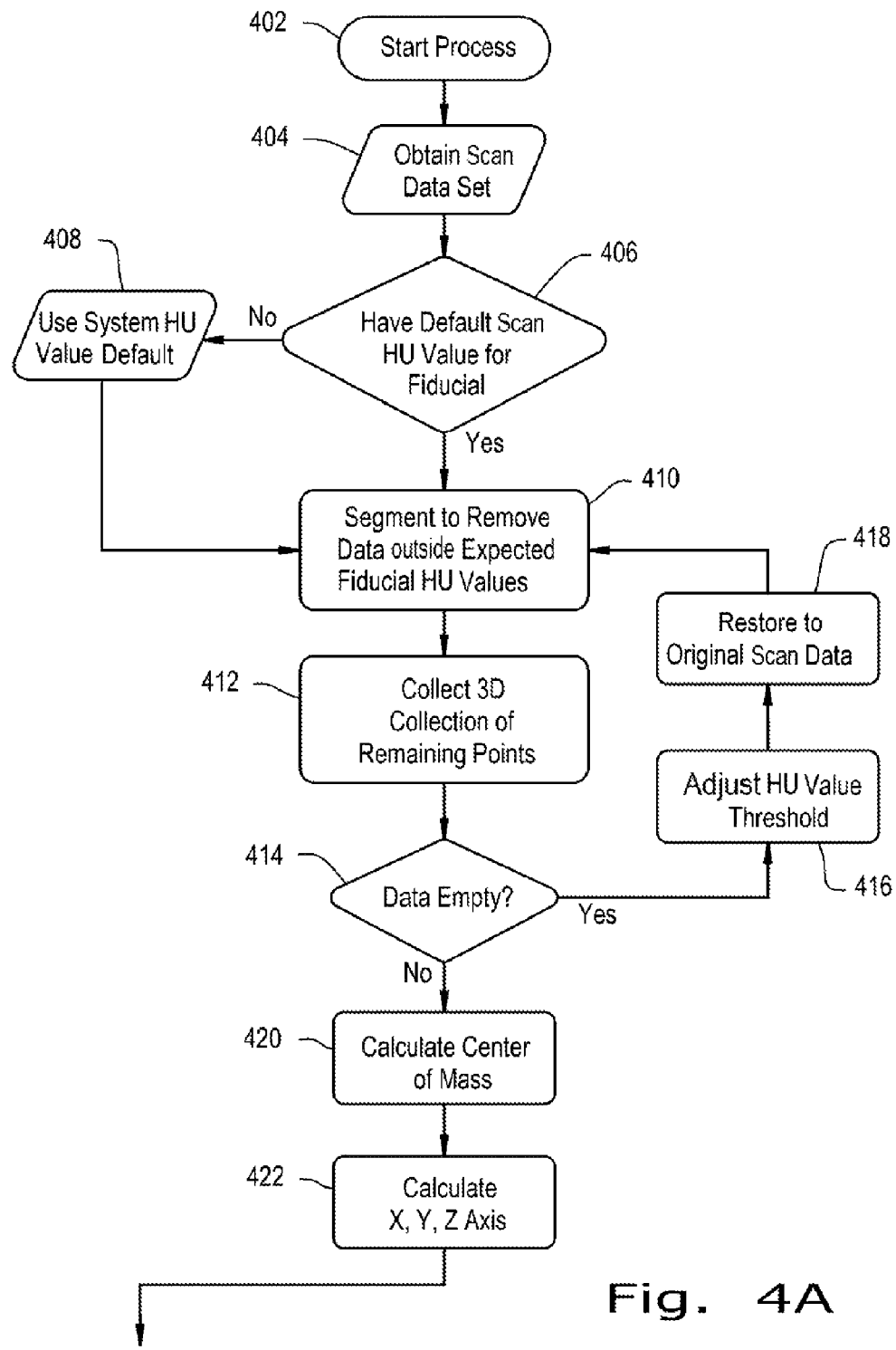
FIGS. 4A-C is a flow chart diagram illustrating one embodiment of the registering method of the present invention.
Figure 4B:
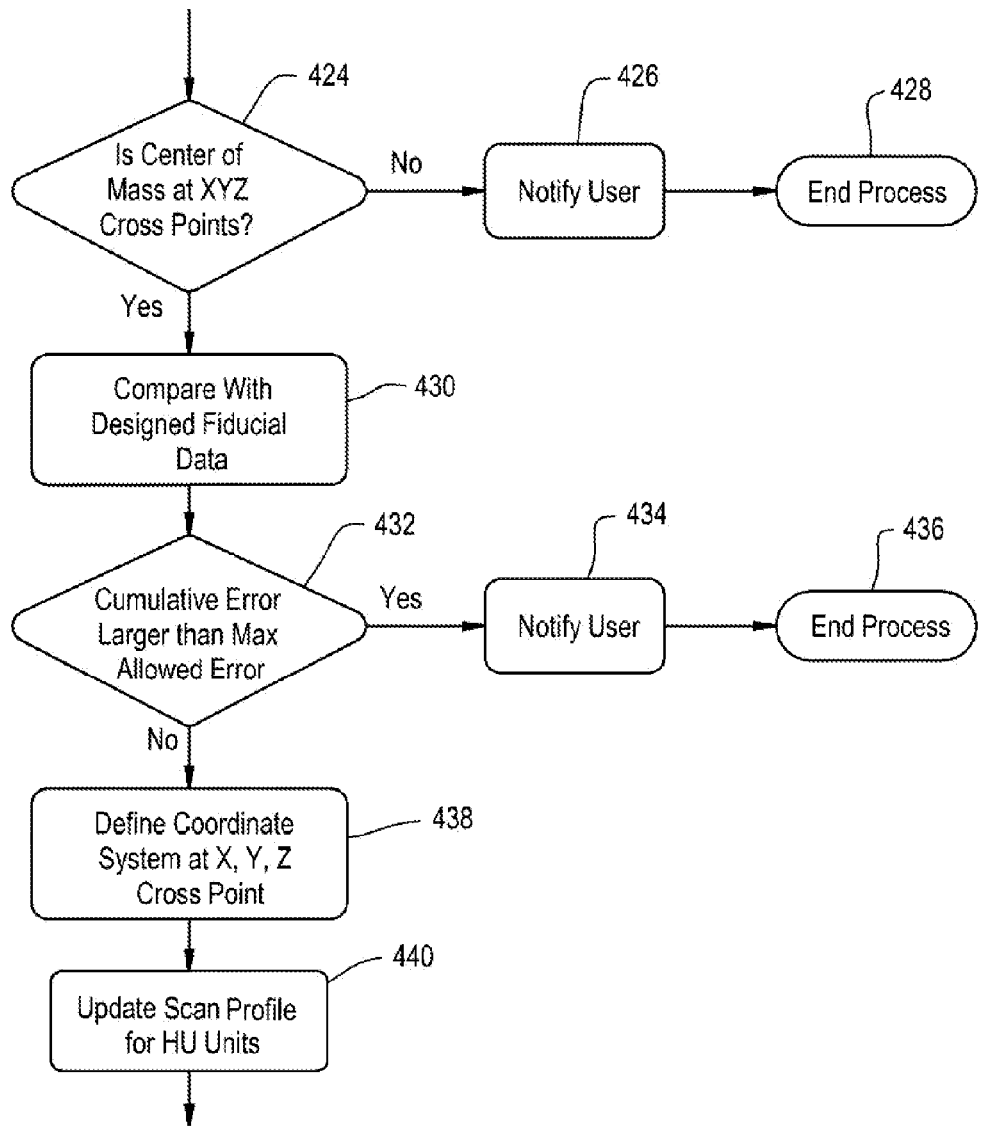
Figure 4C:
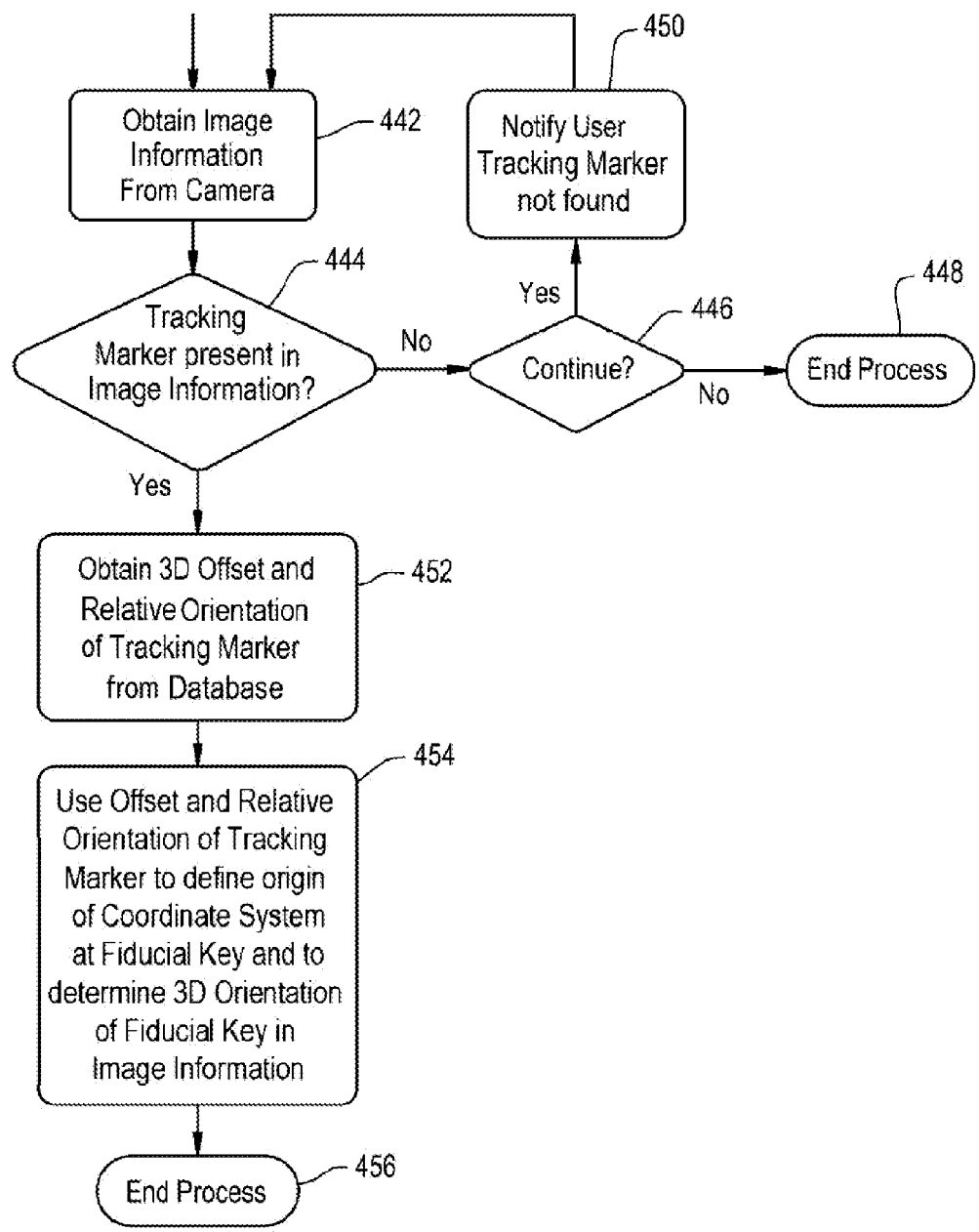

In another aspect there is presented an automatic registration method for tracking surgical activity, as illustrated in FIGS. 4A-C. FIG. 4A and FIG. 4B together present, without limitation, a flowchart of one method for determining the three-dimensional location and orientation of the fiducial reference from scan data. FIG. 4C presents a flow chart of a method for confirming the presence of a suitable tracking marker in image information obtained by the tracker and determining the three-dimensional location and orientation of the fiducial reference based on the image information.

Once the process starts [402], as described in FIGS. 4A and 4B, the system obtains a scan data set [404] from, for example, a CT scanner and checks for a default CT scan Hounsfield unit (HU) value [at 406] for the fiducial which may or may not have been provided with the scan based on a knowledge of the fiducial and the particular scanner model, and if such a threshold value is not present, then a generalized predetermined default value is employed [408]. Next the data is processed by removing scan segments with Hounsfield data values outside expected values associated with the fiducial key values [at 410], following the collection of the remaining points [at 412]. If the data is empty [at 414], the CT value threshold is adjusted [at 416], the original value restored [at 418], and the segmenting processing scan segments continues [at 410]. Otherwise, with the existing data a center of mass is calculated [at 420], along with calculating the X, Y, and Z axes [at 422]. If the center of mass is not at the cross point of the XYZ axes [at 424], then the user is notified [at 426] and the process stopped [at 428]. If the center of mass is at the XYZ cross point then the data points are compared with the designed fiducial data [430]. If the cumulative error is larger than the maximum allowed error [432] then the user is notified [at 434] and the process ends [at 436]. If not, then the coordinate system is defined at the XYZ cross point [at 438], and the scan profile is updated for the HU units [at 440].

Turning now to FIG. 4C, image information is obtained from the tracker, being a suitable camera or other sensor [442]. The image information is two-dimensional and is not required to be a stereo image pair. The image information may be sourced from a single imaging device in the tracker, or may be sourced from multiple imaging devices in the tracker. It bears pointing out that the presence of multiple imaging devices in a tracker does not automatically imply stereo imaging. The image information is analyzed to determine whether a tracking marker is present in the image information [444]. If not, then the user is queried [446] as to whether the process should continue or not. If not, then the process is ended [448]. If the process is to continue, then the user can be notified that no tracking marker has been found in the image information [450], and the process returns to obtaining image information [442]. If a tracking marker has been found based on the image information, or one has been attached by the user upon the above notification [450], the offset and relative orientation of the tracking marker to the fiducial reference is obtained from a suitable database [452]. The term "database" is used in this specification to describe any source, amount or arrangement of such information, whether organized into a formal multi-element or multi-dimensional database or not. A single data set comprising offset value and relative orientation may suffice in a simple implementation of this embodiment of the invention and may be provided, for example, by the user or may be within a memory unit of the controller or in a separate database or memory.

The offset and relative orientation of the tracking marker is used to define the origin of a coordinate system at the fiducial reference and to determine the three-dimensional orientation of the fiducial reference based on the image information [454] and the registration process ends [458]. In order to monitor the location and orientation of the fiducial reference in real time, the process may be looped back from step [454] to obtain new image information from the camera [442]. A suitable query point may be included to allow the user to terminate the process. Detailed methods for determining orientations and locations of predetermined shapes or marked tracking markers from image data are known to practitioners of the art and will not be dwelt upon here. The coordinate system so derived is then used for tracking the motion of any items bearing tracking markers in the proximity of the surgical site. Other registration systems are also contemplated, for example using current other sensory data rather than the predetermined offset, or having a fiducial with a transmission capacity.

Figure 5:
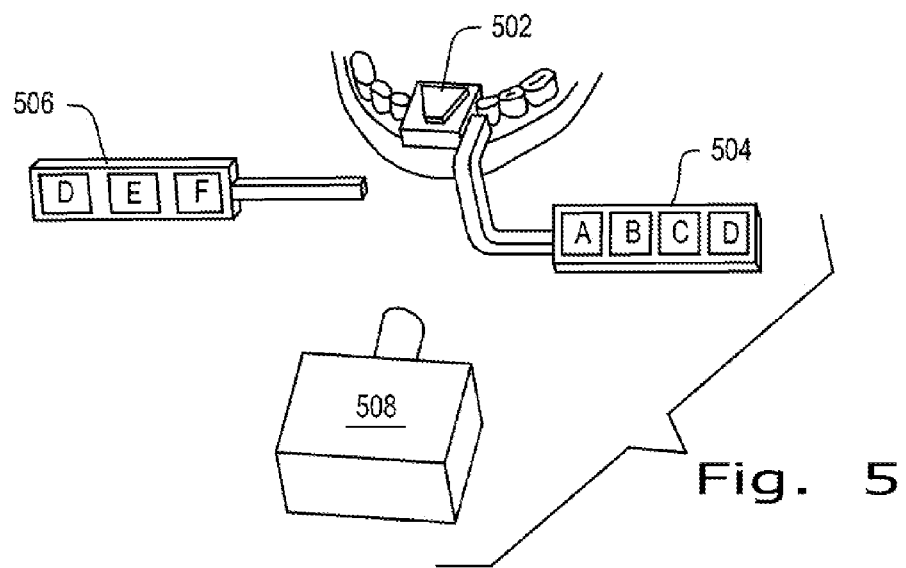
FIG. 5 is a drawing of a dental fiducial key with a tracking pole and a dental drill according to one embodiment of the present invention.

One example of an embodiment of the invention is shown in FIG. 5. In addition to fiducial key 502 mounted at a predetermined tooth and having a rigidly mounted tracking marker 504, an additional instrument or implement 506, for example a hand piece which may be a dental drill, may be observed by a camera 508 serving as tracker of the monitoring system.

Figure 6:
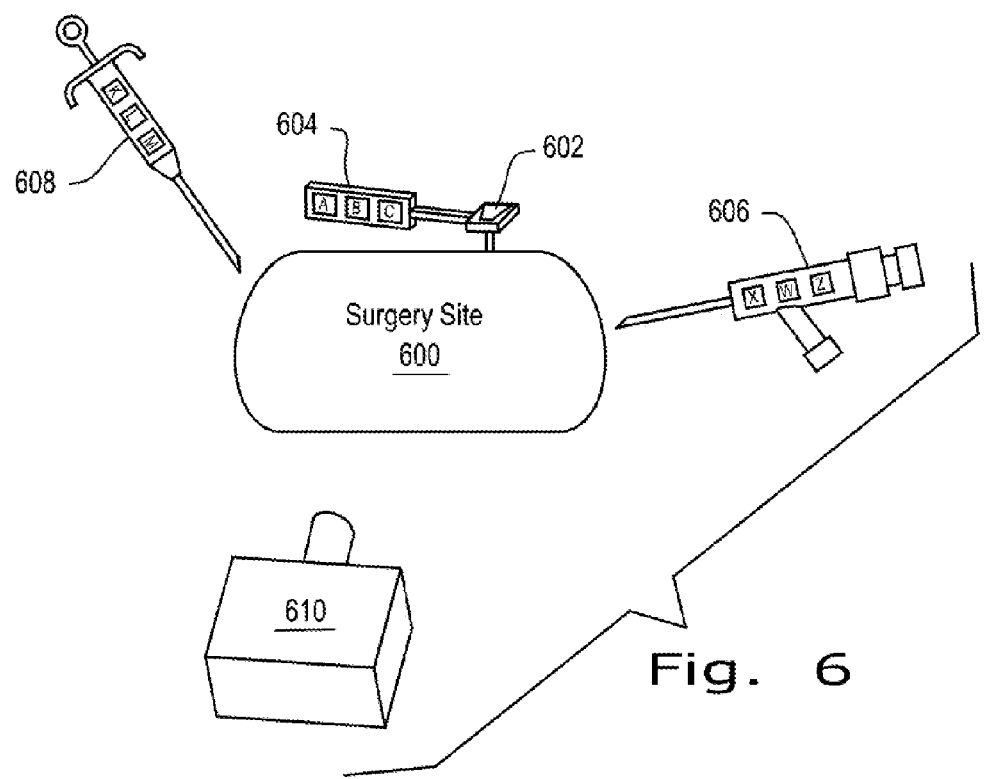
FIG. 6 is a drawing of an endoscopic surgical site showing the fiducial key, endoscope, and biopsy needle according to another embodiment of the invention.

Another example of an embodiment of the invention is shown in FIG. 6. Surgery site 600, for example a human stomach or chest, may have fiducial key 602 fixed to a predetermined position to support tracking marker 604. Endoscope 606 may have further tracking markers, and biopsy needle 608 may also be present bearing a tracking marker at surgery site 600. Sensor 610, may be for example a camera, infrared sensing device, or RADAR.

Figure 7:
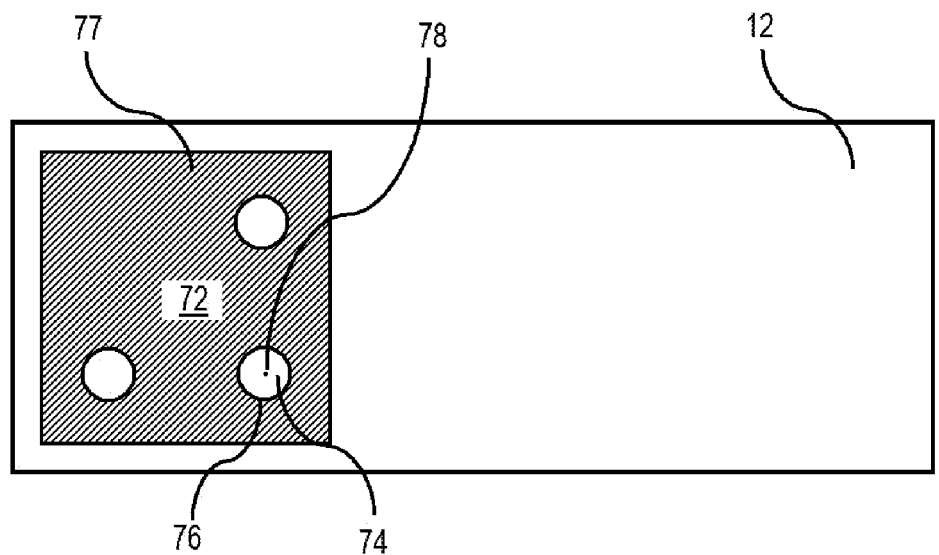
FIG. 7 is a drawing of a tracking marker bearing a pattern tag according to an embodiment of the present invention.

A further aspect of the invention is described at the hand of FIG. 7, which shows in more detail tracking marker 12 of FIGS. 3A and 3B. As stated heretofore, tracking marker 12 may have a particular identifying pattern. In this further aspect of the invention the matter of the particular pattern, shown generally at 72, on tracking marker 12 is addressed in more detail. In a first embodiment shown in FIG. 7 the pattern 72 comprises a plurality of contrasting portions 74. Pattern 72 is further characterized by being rotationally asymmetrical. As a result, an image of the pattern 72 inherently identifies the rotational orientation about an axis perpendicular to the plane of pattern 72 of tracking marker 12. Pattern 72 is further characterized by having at least one contrasting portion 74 that has a perimeter comprising a mathematically describable curved section. In FIG. 7 the simplest case of a circular perimeter 76 is shown, which comprises the entire perimeter. In other embodiments the curved section may constitute less than the entire perimeter and the curve may be, for example, without limitation, a conic section. In yet further embodiments the curve can be a mathematically describable curve other than a conic section. In yet further embodiments, the perimeter may be a mathematically described polygon.

The basis or grounds of the contrast is limited only in that the contrast has to be discernable by the tracker employed in the surgical site monitoring system of the present invention. For example without limitation, the contrast with surrounding areas on the tracking marker 12 may be by virtue of the contrasting portion 74 being a cutout, by virtue of the contrasting portion 74 being a darker or lighter grey tone, by virtue of the contrasting portion 74 being a different hue or saturation, by virtue of the contrasting portion 74 being a different color in any color space, by virtue of the contrasting portion 74 being a different brightness in an infrared image, or any other basis of image contrast.

The pattern 72 may be implemented on a separate pattern tag 77 that is attached or pasted, temporarily or permanently, to the tracking marker 12. Conversely, the pattern tag 77 may be in itself a tracking marker, such as, for example tracking marker 12, so that the tracking marker itself bears pattern 72. The pattern tag 77 may be planar. The pattern tag 77 may be flexible to allow it to return to planarity after being flexibly deformed. The materials of the pattern tag 77 may be, for example without limitation, a polymer or a paper or a mix of both paper and polymer. In other embodiments the tag 77 may be non-flexibly deformable while remaining dimensionally stable. An individual tracking marker may comprise a plurality of pattern tags, each with a pattern of its own, as will be described below.

In some embodiments, the perimeter may be a mathematically described polygon. In other embodiments, the presence of the mathematically describable curved section provides three distinct benefits. Firstly, it overcomes the inherent problem of straight-edged shapes such as squares, rectangles, and parallelograms which exacerbate problems stemming from the finite number and size of pixels available in typical trackers, such as the tracker used in the several embodiments of the present invention. Due to the fact that the pixels have a finite size, the determination of the exact location of a straight line in an image is difficult to do to an accuracy of less than one pixel. A contrasting portion with a straight-line section to its perimeter would inherently suffer from this limitation. By employing a mathematically describable curved section as perimeter 76 of contrasting portion 74 the location of perimeter 76 can inherently be determined more accurately. We do not dwell here upon the methods of determining contrast boundaries in digital images, as the concepts and methods are well described in the art and well known to practitioners of the art.

Secondly, in addition to the aforementioned more accurate determination of the location of the perimeter, the mathematically describable nature of the curve of the perimeter 76 allows a single very accurate contrasting portion reference point 78 to be determined once an image of the pattern 72 is available, showing its contrasting portion 74 and perimeter 76. By way of the circular example of FIG. 7, a useful choice for a contrasting portion reference point 78 may be the center of the circle described by perimeter 76, which in this case is the center of the contrasting portion 74. However, in a more general case, a point other than the center of the circle may be employed as reference to suit the application.

Thirdly, with the mathematical description of a section of the perimeter 76 of contrasting portion 74 known, the rotation of pattern 72 about further axes may be determined To this end, the appearance of the pattern 72 may be expressed in mathematical terms and stored in a database of any kind, including without limitation a digital database. The tracker of the monitoring system may obtain image information about the pattern 72 on a tracking marker 12. By analyzing the image information mathematically using a suitable controller, for example processor 214 and memory 217 of computer 210 of FIG. 2, and comparing with the stored information about the mathematical description of the pattern, the three-dimensional orientation of tracking marker 12 may be determined. If tracking marker 12 has a large enough three-dimensional extent, then suitable patterns of contrasting portions may also be applied to further surfaces of tracking marker 12 to assist in determining the three-dimensional orientation of tracking marker 12. The same approach may be applied in embodiments in which the perimeter is a mathematically described polygon.

The pattern 72 may be selected to be a unique pattern. This allows the pattern tag 77 or the tracking marker 12 to be uniquely identified within the field of view of the tracker. Thus a variety of items, objects, instruments or implements may be tagged with tracking markers bearing pattern tags, or with just pattern tags, thereby to uniquely identify and track such items, objects, instruments or implements and determine their orientations.

Having described this general aspect of the invention at the hand of contrasting portions with simple circular shapes, we turn to other embodiments employing contrasting portions employing other curved shapes. In other embodiments the curve may be, for example any other form of conic section, such as an ellipse or a parabola and may extend all the way around the contrasting portion. In the case of an ellipse, the contrasting portion reference point may be chosen, for example, to lie along the major semi-axis or minor semi-axis of the ellipse. In particular, a useful choice for contrasting portion reference point may be one of the focii of the ellipse. Another useful choice for contrasting portion reference point may be one of the vertices of the ellipse. In this respect it is to be noted that all that is required is a section of an ellipse, long enough for accurate mathematic description, thereby to allow the determination of the various axes and the focii. The contrasting portion therefore does not have to be a complete ellipse. Herein lies the benefit of the curve being mathematically describable. If a parabola is chosen, a useful choice for contrasting portion reference point may be the focus of the parabola, the vertex of the parabola or the point where the axis of symmetry of the parabola crosses the directrix of that parabola.

In yet further embodiments of the invention a mathematically describable curve other than a conic section may be used to describe at least a section of the perimeter of the contrasting portion. Such curves may well be more complex than conic sections and may require careful consideration as regards a suitable contrasting portion reference point. In yet further embodiments of the invention, the contrasting portion can be a mix of the aforementioned conic sections and other shapes. One example is a semicircle, which, despite having only part of its perimeter described by a circle, nevertheless allows all of the benefits of the mathematically described circle.

In yet further embodiments of the invention the pattern may comprise a plurality of contrasting portions of which more than one contrasting portion has a perimeter having a mathematically describable curved section or that is a mathematically describable polygon. A pattern reference point may in such a case be a point expressed relative to the resulting plurality of contrasting portion reference points derived from the more than one contrasting portion. For example without limitation, each of the three contrasting portions of pattern tag 77 in FIG. 7 is a circle and each has its center as contrasting portion reference point. In such a case, the pattern reference point may be, for example, given by a point exactly at the middle of the line joining the centers of the two unnumbered contrasting portions. Any other useful point may be selected for this purpose, including the contrasting portion reference point 78 or any of the corners of the pattern tag 77.

Figure 8:
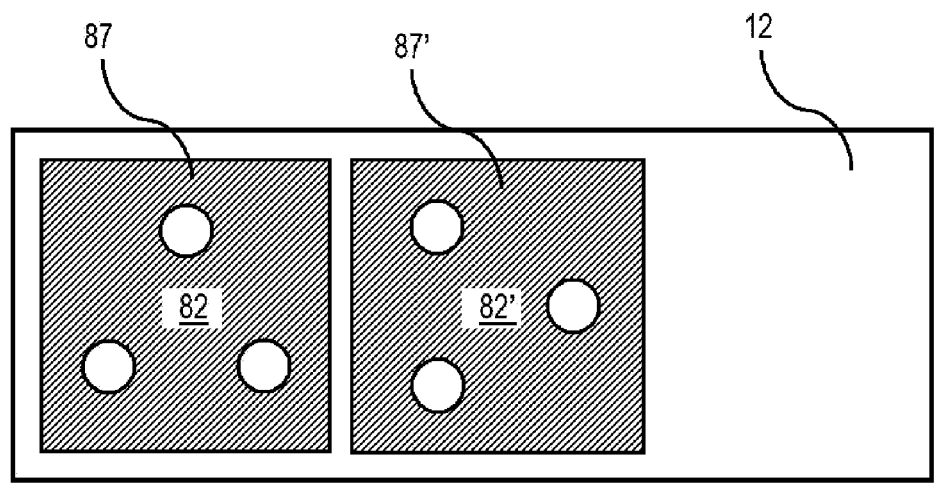
FIG. 8 is a drawing of tracking marker bearing two pattern tags according to another embodiment of the present invention.

In a further implementation shown in FIG. 8, tracking marker 12 may comprise more than one pattern tag, for example pattern tag 87 and pattern tag 87', with each pattern tag 87 and 87' individually having a pattern shown generally at 82 and 82' respectively and each having rotational symmetry, while the combination of patterns 82 and 82' is rotationally asymmetrical. In this particular implementation the two tags are identical, but, in a general case, are located on tracking marker rotated with respect to each other. This has the benefit of requiring only one kind of patterned tag. It reduces costs and also lowers the management burden during practical use, as only one kind of tag needs to be kept at hand for in, for example, surgery. In another embodiment, the two pattern tags 87 and 87' may be arranged next to each other on tracking marker 12 in identical orientations. This still provides a resulting pattern that is rotationally asymmetric. In FIG. 8 the two pattern tags 87 and 87' are shown as being attached in coplanar fashion. In other embodiments they are not limited to being coplanar.

Figure 9:
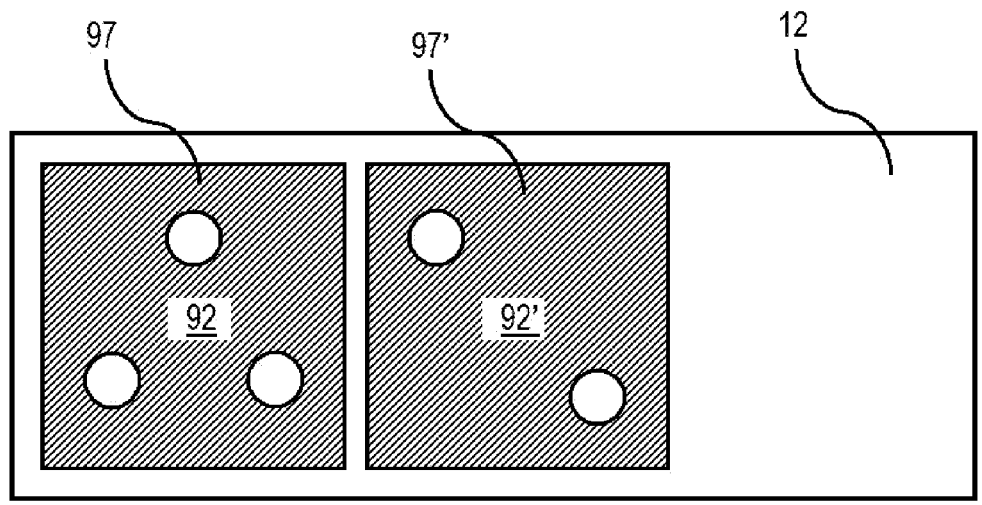
FIG. 9 is a drawing of tracking marker bearing two pattern tags according to a further embodiment of the present invention.

In a further implementation shown in FIG. 9 two pattern tags 97 and 97' are employed and both have some form of rotational symmetry. Pattern tag 97 has a pattern 92 with rotational symmetry of 120 degrees while pattern tag 97' has a pattern 92' that differs from pattern 92 and has a rotational symmetry of 180 degrees. The two pattern tags 97 and 97' together, however, provide rotational asymmetry.

Figure 10:
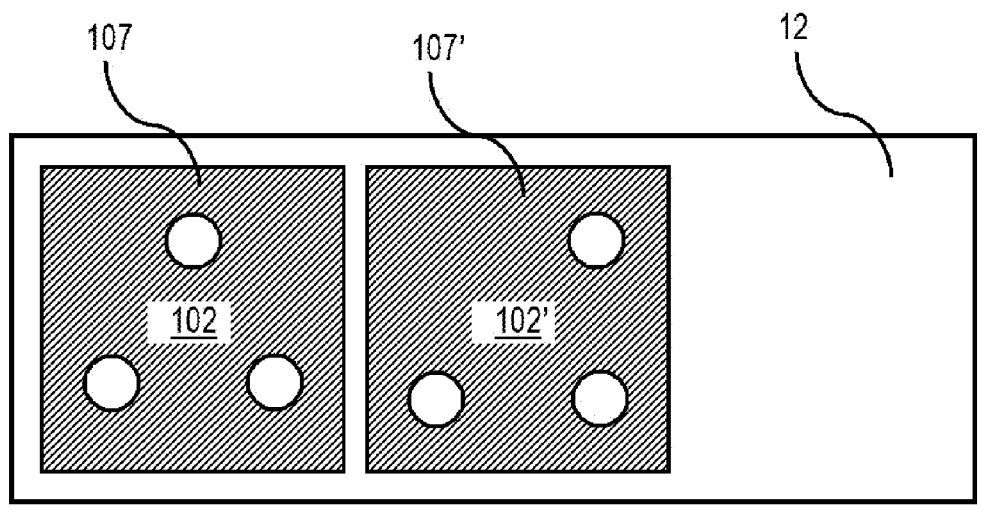
FIG. 10 is a drawing of tracking marker bearing two pattern tags according to yet a further embodiment of the present invention.

In FIG. 10 is presented yet a further implementation based on the pattern 102 of pattern tag 107 having rotational symmetry and the pattern 102' of pattern tag 107' being rotationally asymmetrical. The joint patterns 102 and 102' constitute a rotationally asymmetrical pattern.

In FIGS. 7-10 very simple patterns have been used as examples. The patterns may be chosen to be more complex and thereby more unique. This allows the pattern tags to be uniquely identified within the field of view of the tracker. Thus, a variety of items, objects, instruments or implements may be tagged with pattern tags, thereby to uniquely identify and track such items, objects, instruments or implements and determine their orientations. The sets of two pattern tags of FIGS. 8-10 can in each embodiment of the invention constitute a single tracking marker. Yet further suitable patterns are discussed below at the hand of FIGS. 15 to 18.

The patterns 82, 82', 92, 92', 102, 102' of FIGS. 8-10 may be implemented on separate pattern tags that are attached or pasted, temporarily or permanently, to tracking marker 12. Conversely, the pairs of pattern tags (87, 87'), (97, 97'), and (107, 107') may in themselves be tracking markers, such as, for example tracking marker 12, so that the tracking markers themselves bear patterns (82, 82'), (92, 92'), and (102, 102'), respectively. The pattern tags may be planar. The pattern tags may be flexible to allow them to return to planarity after being flexibly deformed. The materials of the pattern tags may be, for example without limitation, a polymer or a paper, or a mix of both paper and polymer. In other embodiments, the pattern tags may be non-flexibly deformable while remaining dimensionally stable.

The automatic registration method for tracking surgical activity already described at the hand of FIGS. 4A-C may employ the tracking marker of FIGS. 7-10 bearing the pattern tags and or patterns described at the hand of FIGS. 7-10. In the method of FIG. 4A the offset and relative orientation of the tracking marker to the fiducial reference is obtained from a suitable database in method step [452]. If the tracking marker, pattern tags and patterns of FIGS. 7-10 are employed, then the database in question is pre-supplied with information concerning the tracking marker 12, the pattern tags 77, 87, 87', 97, 97', 107, 107', the patterns 72, 82, 82', 92, 92', 102, 102' and the contrasting portions, for example contrasting portion 74, of the pattern tags. The information comprises, in particular, the mathematical descriptions of curved sections or polygons of the perimeters of the contrasting portions of the pattern tags, for example perimeter 76. It may also comprise the locations of contrasting portion reference points, for example contrasting portion reference point 78, and pattern reference points for pattern tags that are be employed. The term "geometric information" is employed in the present specification to describe this collection of information regarding the shapes, sizes, perimeters, curved perimeter sections and the like of the contrasting portions of the pattern tags, along with the information on the patterns on the various pattern tags attached to the tracking markers and the associated locations of contrasting portion reference points and pattern reference points. The geometric information specifically comprises a mathematical description of at least a section of the perimeter of at least one contrasting portion on any given pattern tag. The geometric information may also include the known spatial and orientational relationship between the pattern tags and the tracking markers.

Figure 11:
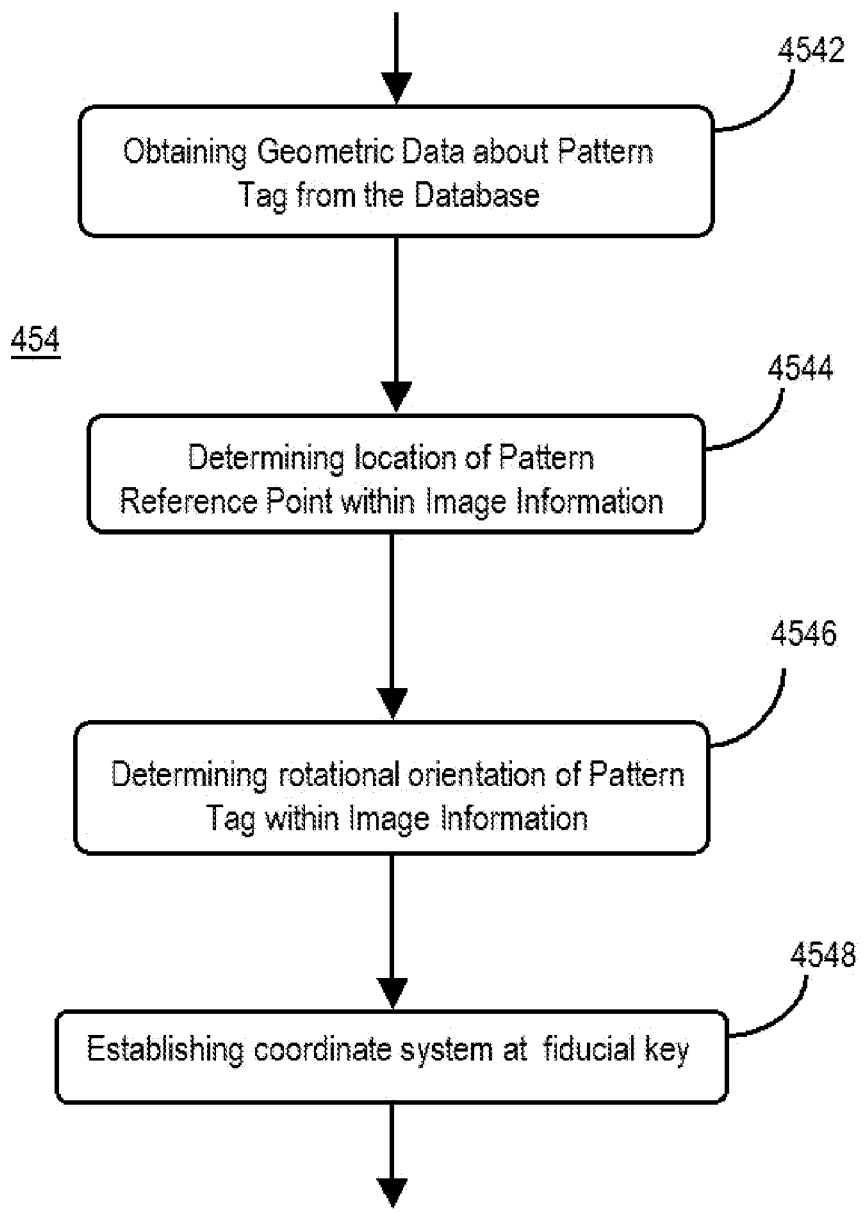
FIG. 11 is a drawing of a flow chart for a method of establishing a coordinate system at a fiducial key according to an embodiment of the present invention.

The automatic registration method for tracking surgical activity as per the present embodiment employing the pattern tags (for example pattern tag 77) as described herein comprises the steps [402] to [456] of FIGS. 4A-C. In step [444] of FIG. 4C tracking marker 12 has already been identified on the basis of its unique pattern as per FIGS. 7-10. Step 454 of FIG. 4C will now be described in more detail at the hand of FIG. 11. The using [454] the offset and relative orientation of tracking marker 12 to define an origin of a coordinate system at fiducial key 10 and to determine the three-dimensional orientation of fiducial key 10 in image information, as shown in FIG. 4C, comprises the following steps in FIG. 11. The process starts with the controller, for example processor 214 and memory 217 of computer 210 of FIG. 2, obtaining [at 4542] from the database geometric information about at least one pattern tag (for example pattern tag 77) associated with the tracking marker 12, the controller determining [at 4544] within the image information the location of at least one of the pattern reference points of the at least one pattern tag 77 based on the geometric information, and the controller determining [at 4546] within the image information the rotational orientation of the at least one pattern tag (for example pattern tag 77) based on the geometric information. With the relationship of the pattern reference point to tracking marker pre-established within the geometrical information, and the offset and relative orientation of the tracking marker 12 with respect to fiducial key 10 known (see step in FIG. 4C), a coordinate system is established [at 4548] at the fiducial key 10.

The rotationally asymmetrical tracking marker arrangements described here can be applied to other fields of general machine vision and product tracking beyond the field of surgery. More specifically, while tracking marker 12 has been described in terms of being attached to a fiducial key 10 by a tracking pole 11 (see for example FIG. 3B), the patterned tracking markers of the present invention may be applied in other fields without the use of fiducials and tracking poles, in which case they are useful in determining the physical spatial orientation of items bearing the patterned tracking markers. By way of example, a flexible pattern tag may be applied to a cylindrical surface of an object, such as a can in the food industry. With the pattern reference point known and with the mathematical description of the pattern known, the position of the can and the curvature of the pattern tag may respectively be determined from image information obtained using a suitable tracker.

Figure 12:
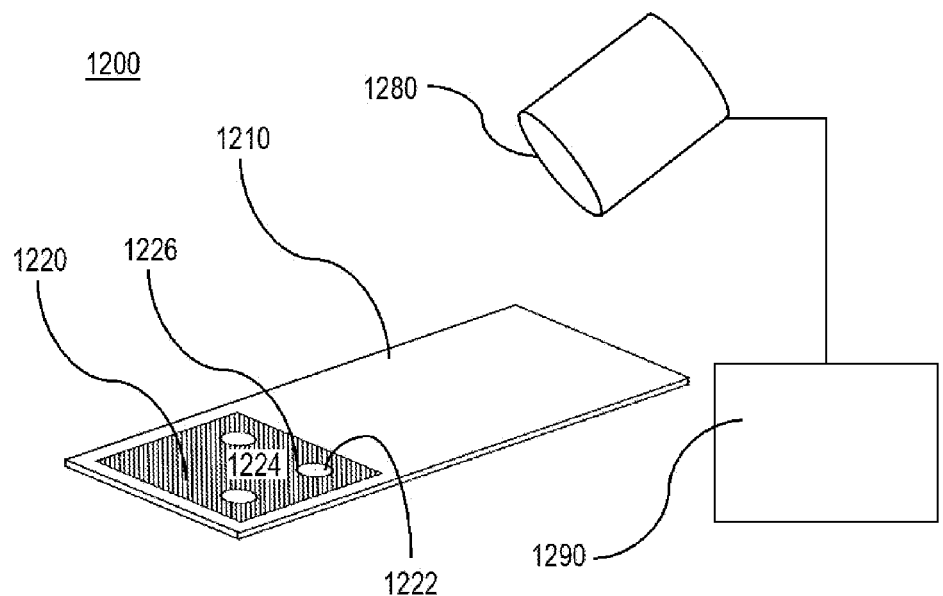
FIG. 12 is a drawing of a three-dimensional position and orientation tracking system according to an embodiment of the present invention.

In a further embodiment of the present invention, shown schematically in FIG. 12, a three-dimensional position and orientation tracking system, shown generally at 1200, comprises at least one pattern tag 1220 attached to an item 1210, the pattern tag 1220 comprising a plurality of contrasting portions 1222. The system 1200 further comprises a tracker 1280 configured for obtaining image information about the at least one pattern tag 1220; a database comprising geometric information describing a pattern 1224 on the at least one pattern tag 1220; and a controller 1290, for example processor 214 and memory 217 of computer 210 of FIG. 2. The controller 1290 is configured for receiving and processing the image information from the tracker 1280; accessing the database to retrieve geometric information about the at least one pattern tag 1220; and comparing the image information with the geometric information. The plurality of contrasting portions 1222 are arranged in a rotationally asymmetric pattern 1224 and at least one of the plurality of contrasting portions 1222 has a perimeter 1226 comprising a mathematically describable curved section. The perimeter 1226 of the at least one contrasting portion 1222 may comprise a conic section including, for example without limitation, an ellipse or a circle. The at least one pattern tag 1220 may be flexible. The at least one pattern tag 1220 may be substantially planar.

Figure 13:
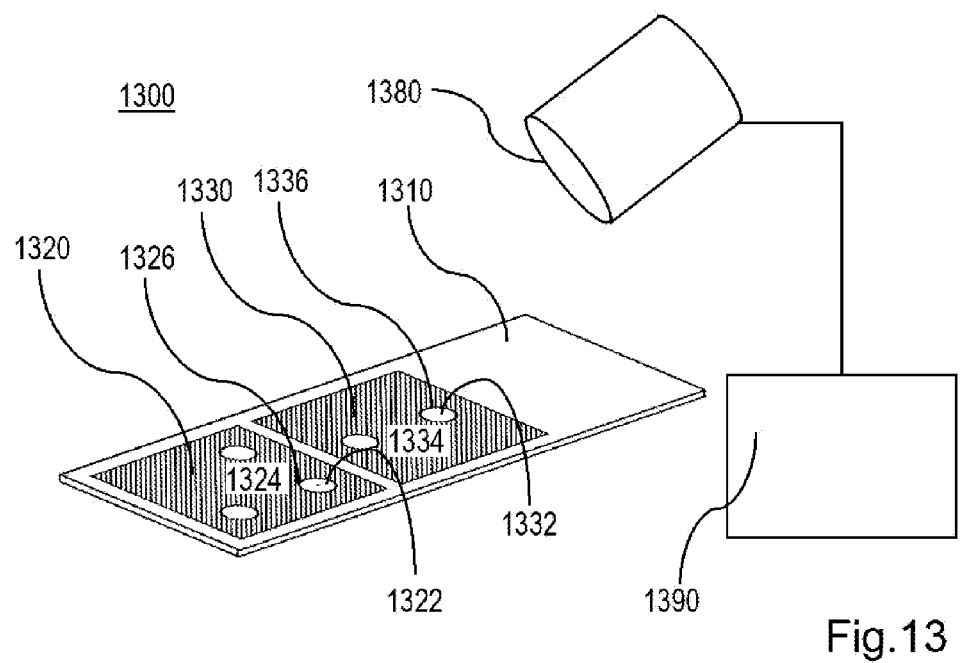
FIG. 13 is a drawing of a three-dimensional position and orientation tracking system according to another embodiment of the present invention.

In another embodiment of the present invention, shown schematically in FIG. 13, the three-dimensional position and orientation tracking system, shown generally at 1300, may comprise at least two pattern tags attached to an item 1310, a first of the at least two pattern tags, shown in FIG. 13 as pattern tag 1320, comprising a first plurality of contrasting portions 1322 and a second of the at least two pattern tags, shown in FIG. 13 as pattern tag 1330, comprising at least one contrasting portion 1332; a tracker 1380 configured for obtaining image information about the at least two pattern tags 1320 and 1330, a database comprising pattern tag information describing the appearance of the at least two pattern tags; and a controller 1390, for example processor 214 and memory 217 of computer 210 of FIG. 2. The controller 1390 is configured for receiving and processing the image information from the tracker 1380; accessing the database to retrieve geometric information about at least two pattern tags 1320 and 1330; and comparing the image information with the geometric information. At least one of the first and second pattern tags, taken to be 1330 in FIG. 13, has one or more contrasting portions 1332 arranged in a rotationally symmetric pattern 1334; the contrasting portions 1322 and 1332 of respectively the first and second pattern tags 1320 and 1330 together constitute a rotationally asymmetric pattern; and at least one contrasting portion 1322, 1332 respectively of each of the at least two pattern tags 1320, 1330 has a perimeter 1326, 1336, comprising a mathematically describable curved section.

In respect of the two embodiments exemplified in FIGS. 12 and 13, simple patterns have been used as examples. The patterns may be chosen to be more complex and thereby more unique. This allows the pattern stages to be uniquely identified within the field of view of the tracker. Thus a variety of items, objects, instruments or implements may be tagged with pattern tags, thereby to uniquely identify and track such items, objects, instruments or implements and determine their orientations.

Figure 14:
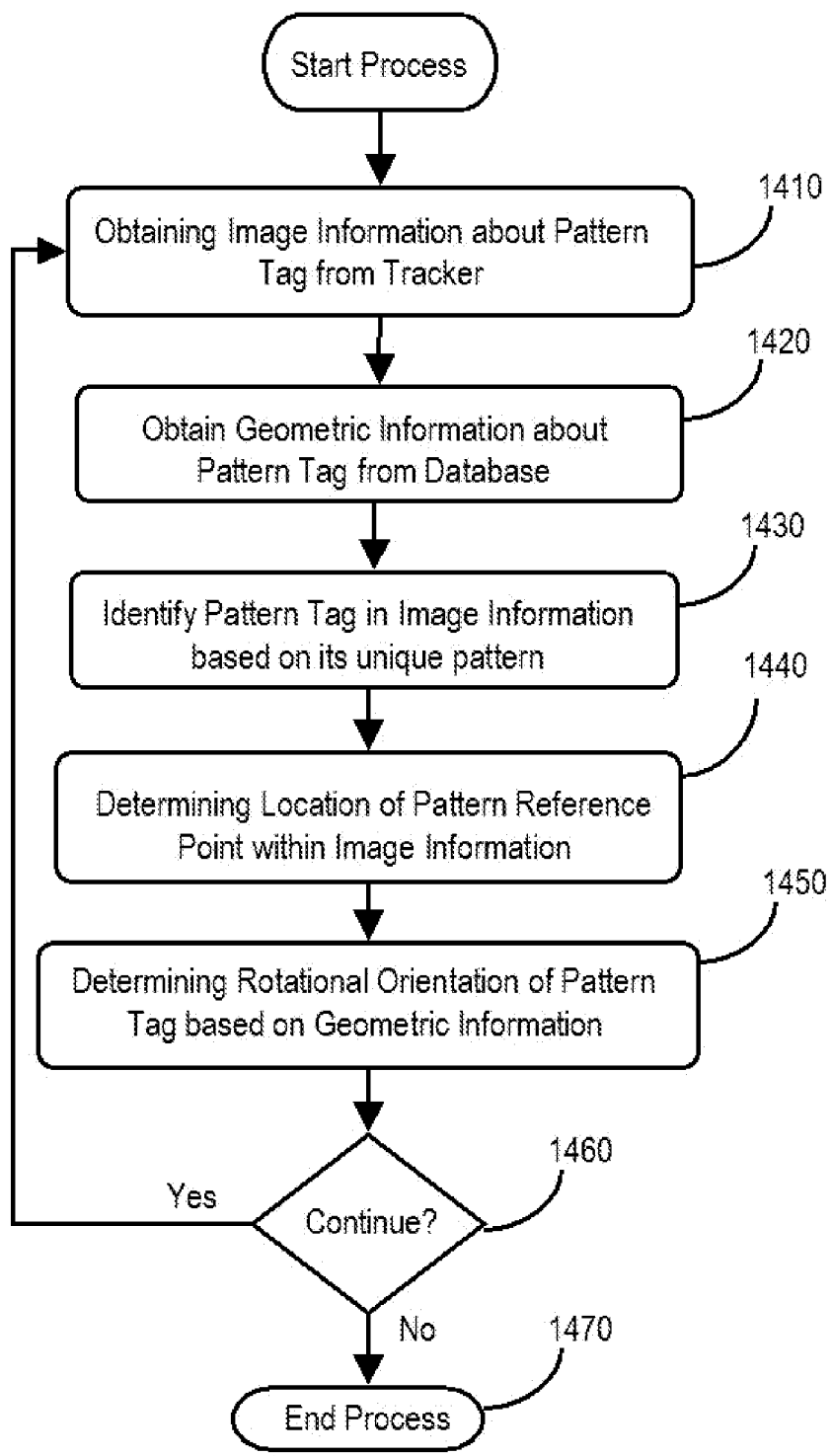
FIG. 14 is a drawing of a flow chart describing a method for tracking an item bearing a pattern tag.

In a further aspect of the invention, described at the hand of FIG. 14, a method is provided for tracking an item bearing at least one pattern tag, for example pattern tag 1220, 1320, or 1330 of FIGS. 12 and 13. The method comprises a suitable controller 1290, 1390 (comprising for example processor 214 and memory 217 of computer 210 of FIG. 2) obtaining [at 1410] from a suitable tracker, for example tracker 1280 of FIG. 12 or tracker 1380 of FIG. 13, image information about the at least one pattern tag. The method further comprises the controller 1290 or 1390 obtaining [at 1420] from a suitable database geometric information about the at least one pattern tag (for example pattern tag 77), the controller identifying [at 1430] the at least one pattern tag on the basis of its unique pattern, and the controller determining [at 1440] within the image information the location of at least one pattern reference point of the at least one pattern tag based on the geometric information, the geometric information specifically comprising a mathematical description of at least a section of the perimeter 1226, 1326, 1336 of at least one contrasting portion 1222, 1322, 1332 of the at least one pattern tag. The method further comprises the controller determining [at 1450] within the image information the rotational orientation of the at least one pattern tag based on the geometric information. Having located the at least one pattern reference point and having determined the rotational orientation of the at least one pattern tag, the user is queried [at 1460] as to whether the process should continue or not. If not, then the process is ended [at 1470]. If the process is to continue, then the process returns to obtaining refreshed image information [at 1410].

The patterns 72, 82, 82', 92, 92', 102, 102' of FIGS. 7-10 are all shown confined within contrasting backgrounds that are rectangular. In particular, in FIGS. 7-10 the patterns 72, 82, 82', 92, 92', 102, 102' are shown as confined within contrasting backgrounds that are squares, which form a subset of rectangles. In yet other embodiments, the patterns, as identified by their contrasting portions, may be confined or configured within general non-square contrasting backgrounds. We employ the term "non-rectangularly confined contrasting portion" to describe a contrasting portion of pattern not confined to a rectangular contrasting background. Since a square is a rectangular shape, patterns not confined to a rectangular contrasting background, are inherently also not confined to a square background. By way of example, a non-rectangular contrasting background may be a parallelogram as in FIG. 15, or triangular as in FIG. 16, or any other generalized shape.

Figure 15:
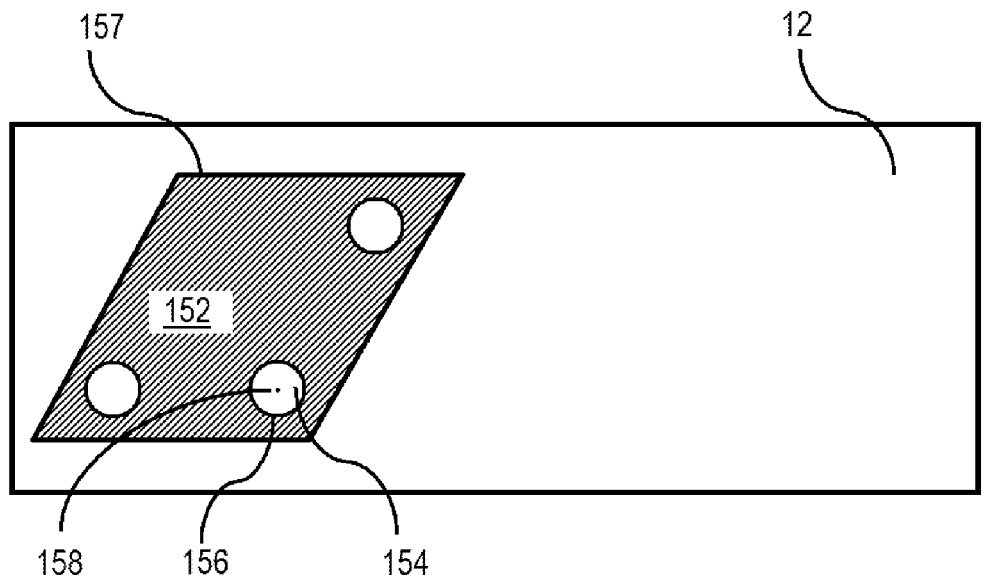
FIG. 15 is a drawing of a pattern on tracking marker of the present invention confined by a contrasting background with a parallelogram shape.

In FIG. 15, pattern 152 on tracking marker 12 is confined by a contrasting background 157 having a parallelogram shape. Pattern 152 is rotationally asymmetrical. Parallelogram 157 may be the shape of the pattern tag employed, or may be a contrasting background on tracking marker 12 itself, or may be a background on part of a pattern tag. Contrasting portion 154 has a contrasting portion reference point 158, which is the center of contrasting portion 154 in this example embodiment. Contrasting portion 154 has a perimeter 156 that is describable by a mathematical function, being a circle in this example embodiment.

Figure 16:
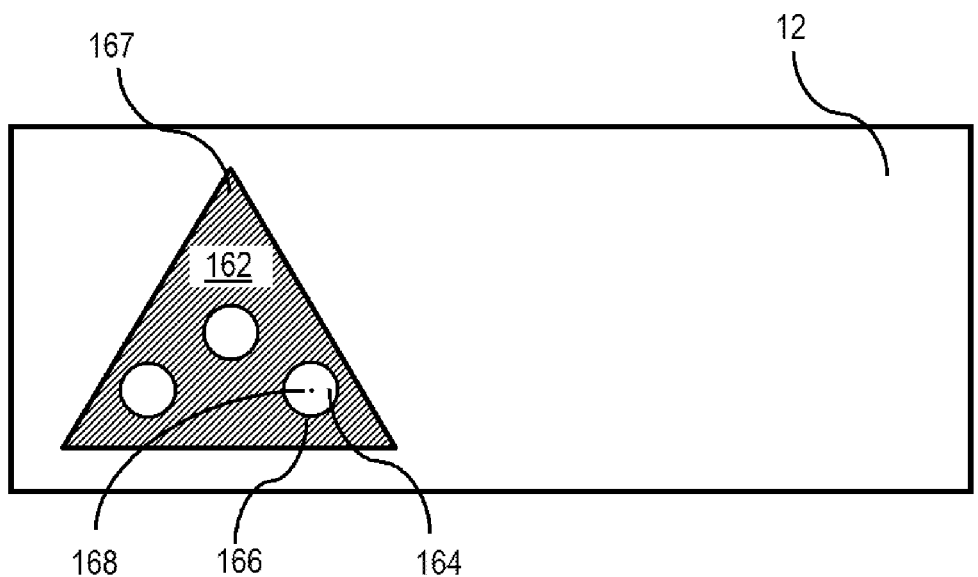
FIG. 16 is a drawing of a pattern on tracking marker of the present invention confined by a contrasting background with a triangular shape.

In FIG. 16, pattern 162 on tracking marker 12 is confined by contrasting background 167 having a triangular shape. Pattern 162 is rotationally asymmetrical. Triangle 167 may be the shape of the pattern tag employed, or may be a contrasting background on tracking marker 12 itself, or may be a background on part of a pattern tag. Contrasting portion 164 has contrasting portion reference point 168, which is the center of contrasting portion 164 in this example embodiment. Contrasting portion 164 has perimeter 166 that is describable by a mathematical function, being a circle in this illustrative embodiment.

Figure 17:
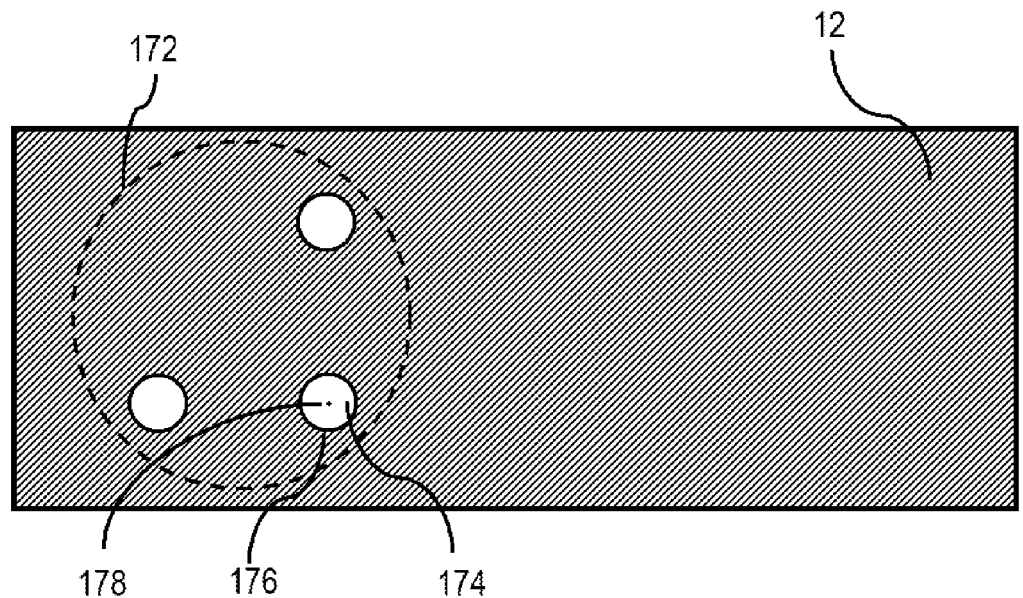
FIG. 17 is a drawing of an unconfined pattern on a tracking marker of the present invention.

In yet further embodiments the patterns, as identified by their contrasting portions, may be on backgrounds that have no particular confining perimeter and may simply be on a contrasting background of a shape that is not predetermined. The background may be the surface of the tracking marker 12 or be part of the tagged item itself. We employ the term "unconfined contrasting portion" to describe a contrasting portion of a pattern having no predetermined confinement. FIG. 17 provides an example of tracking marker 12 bearing, either directly on itself or on a pattern tag attached to it, unconfined pattern 172. Pattern 172 is rotationally asymmetrical. Contrasting portion 174 has contrasting portion reference point 178, which is the center of contrasting portion 174 in this example embodiment. Contrasting portion 174 has perimeter 176 that is describable by a mathematical function, being a circle in this example embodiment.

Figure 18:
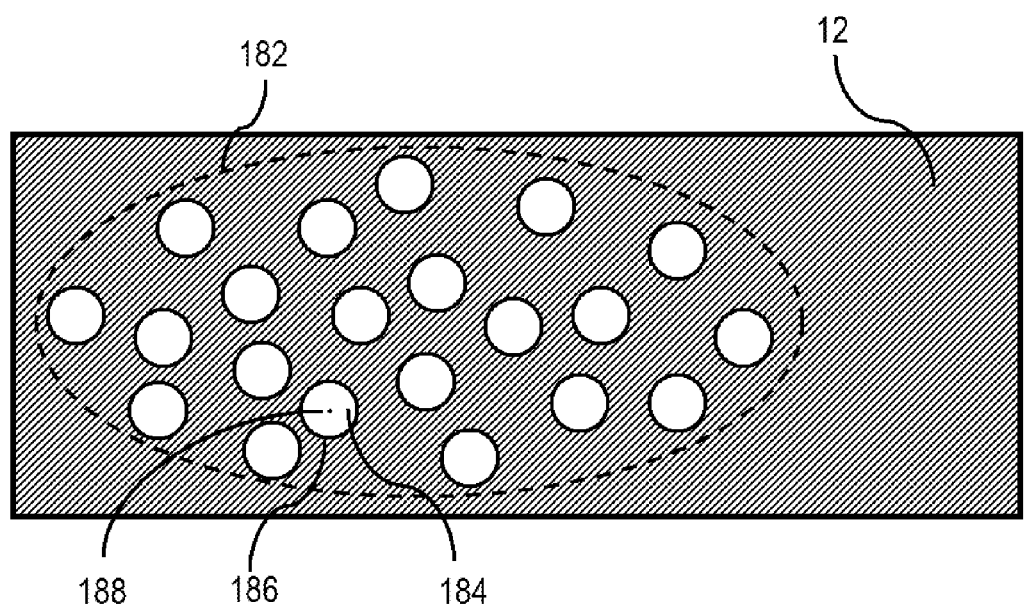
FIG. 18 is a drawing of an unconfined pattern with a random distribution on a tracking marker of the present invention.

In FIGS. 3K, 3L, 7, 8, 9, 10, 15, 16 and 17 the patterns 313, 323, 72, 82, 82', 92, 92', 102, 102', 152, 162 and 172 are shown as comprising dots, or, in a more general case, other shapes, distributed on grid points, the grid points themselves having a distinct predetermined distribution, the dots being either present or absent at the grid points. In a further embodiment, the dots or other elements constituting the patterns may be randomly distributed, the random distribution being included in the geometric information employed to identify and orient the tracking marker. The use of random distributions of contrasting portions helps to ensure that the patterns on pattern tags are more specifically unique and do not have rotational symmetry. Furthermore, the larger the number of contrasting portions, the more accurate the location and orientation of the tracking marker can be determined. Mathematical and other methods for generating random spatial distributions are well known in the art and will not be further dwelt upon here. FIG. 18 shows an example of a tracking marker 12 bearing, either directly on itself or on a pattern tag attached to it, unconfined pattern 182 having a random distribution of contrasting portions 184. Contrasting portion 184 has contrasting portion reference point 188, which is the center of contrasting portion 184 in this example embodiment. Contrasting portion 184 has perimeter 186 that is describable by a mathematical function, being a circle in this illustrative embodiment.

If the tracking marker, pattern tags and patterns of FIGS. 15-18 are employed, then the database in question is pre-supplied with information concerning the tracking marker 12, the pattern tags 157, 167, 177, 187; the patterns 152, 162, 172, 182; and the contrasting portions, for example contrasting portion 154, of the pattern tags. The information comprises, in particular, the mathematical descriptions of curved sections of the perimeters of the contrasting portions of the pattern tags, for example perimeter 156. It may also comprise the locations of contrasting portion reference points, for example contrasting portion reference point 158, and pattern reference points for pattern tags that are be employed.

In embodiments in which the pattern on the pattern tag has a random distribution, the geometric information comprises predetermined distribution information describing the random distribution of the contrasting portions of the pattern on the pattern tag. In these embodiments, the determining of the three-dimensional location of the at least one pattern reference point and the determining of the three-dimensional orientation of the tracking marker both comprise comparing the image information from the tracker with the predetermined distribution information within the geometric information.

Figure 19:
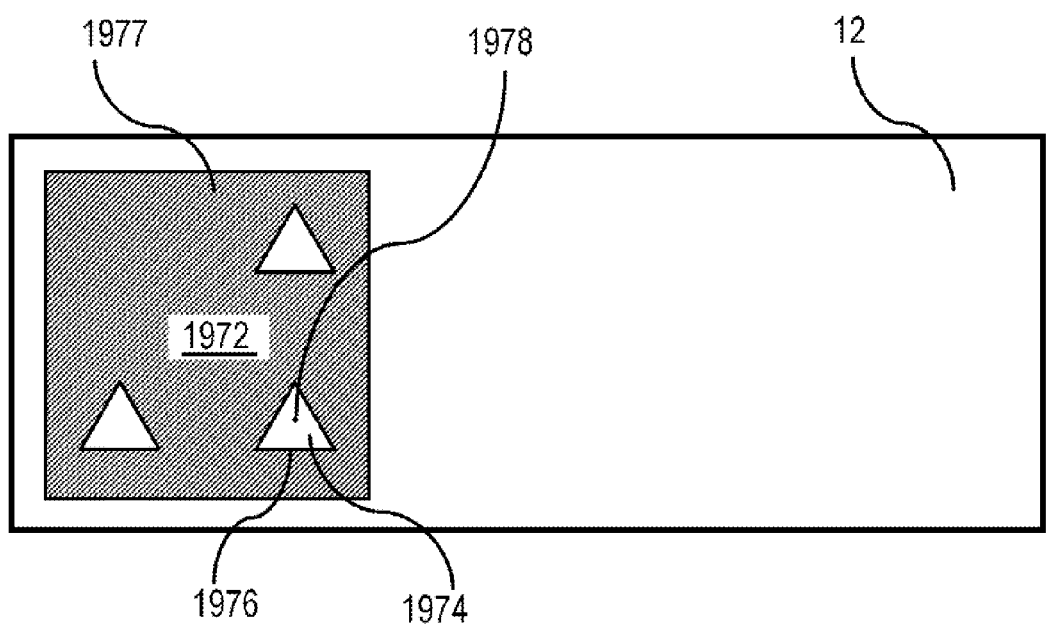
FIG. 19 is a drawing of a tracking marker bearing a pattern tag according to another embodiment of the present invention.

Another embodiment of tracking marker 12 of FIGS. 3A and 3B is described in more detail at the hand of FIG. 19. As stated heretofore, tracking marker 12 may have a particular identifying pattern. The particular pattern, shown generally at 1972, comprises a plurality of contrasting portions 1974. As with pattern 72 of FIGS. 7-10, pattern 1972 is further characterized by being rotationally asymmetrical. As a result, an image of the pattern 1972 inherently identifies the rotational orientation about an axis perpendicular to the plane of pattern 1972 of tracking marker 12. Pattern 1972 is further characterized by having at least one contrasting portion 1974 that has a perimeter having a mathematically describable polygonal shape. In FIG. 19, the perimeter 1976 is shown as having a triangular shape in particular. In other embodiments the mathematically describable geometric shape may be any polygonal shape, including but not limited to a square, a rectangle, a parallelogram, a pentagon, a hexagon, or any other polygon. In a more general implementation, the geometric shape may be a distorted geometrical structure in which one or more of the sides of the geometrical shape has a different length from any other of the sides of the geometrical shape.

The pattern 1972 may be implemented on a separate pattern tag 1977 that is attached or pasted, temporarily or permanently, to the tracking marker 12. Conversely, the pattern tag 1977 may be in itself a tracking marker, such as, for example tracking marker 12, so that the tracking marker itself bears pattern 1972. The pattern tag 1977 may be planar. The pattern tag 1977 may be flexible to allow it to return to planarity after being flexibly deformed. The materials of the pattern tag 1977 may be, for example without limitation, a polymer or a paper or a mix of both paper and polymer. In other embodiments the tag 1977 may be non-flexibly deformable while remaining dimensionally stable. An individual tracking marker may comprise a plurality of pattern tags, each with a pattern of its own, as will be described below.

In this embodiment, as with those described at the hand of FIGS. 7-18 and the associated method, the database in question is pre-supplied with information concerning the tracking marker 12, any pattern tags on tracking marker 12, the patterns (for example pattern 1972); and the contrasting portions, for example contrasting portion 1974, of the pattern tags. The information comprises, in particular, mathematical descriptions of the perimeters of the contrasting portions of the pattern tags, for example perimeter 1976. It may also comprise the locations of contrasting portion reference points, for example contrasting portion reference point 1978, and pattern reference points for pattern tags that are be employed. In FIG. 19, reference point 1978 is taken to be the centre of contrasting portion 1974 bounded by triangle 1976 as perimeter.

In terms of structure, method, use, and operation, all the concepts described at the hand of FIGS. 7-18 also apply to this embodiment, with the only difference being that the perimeters of the contrasting portions are mathematically describable polygonal shapes.

While this invention has been described as having an exemplary design, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

What is claimed is:
1. A three-dimensional position and orientation tracking system comprising:
   a tracking marker bearing at least one pattern tag comprising a plurality of contrasting portions, at least one of the plurality of contrasting portions having a polygonal shape, the tracking marker having a shape with a surface that extends in three dimensions,
   a tracker configured for obtaining image information about the at least one pattern tag;
   a database comprising geometric information, the geometric information containing a pattern on the at least one pattern tag and a mathematical description of the polygonal shape of the contrasting portions; and
   a controller having a processor and memory, the controller in communication with the tracker and the database, the memory storing software that when executed by the processor is configured to receive and process the image information from the tracker; access the database to retrieve the geometric information; and compare the image information with the geometric information to identify and obtain a three-dimensional orientation and a three-dimensional location of the at least one pattern tag.

2. The system of claim 1, further including a display in communication with the controller, the controller further including software that when executed by the processor displays one of the position of the at least one pattern tag in the image information from the tracker, potential trajectories of the pattern tag, and boundary conditions relating to the at least one pattern tag.

3. The system of claim 1, wherein the controller further includes software that when executed by the processor creates a model based on a previous scan and image information from the tracker, said system further comprising a display in communication with the controller and the controller includes further software that when executed by the controller displays the position of the at least one pattern tag within the model on the display.

4. The system of claim 1, wherein the perimeter of the at least one contrasting portion is a square.

5. The system of claim 1, wherein the perimeter of the at least one contrasting portion is a triangle.

6. The system of claim 1, wherein the perimeter of the at least one contrasting portion is a hexagon.

7. The system of claim 1, wherein the at least one pattern tag comprises a flexible material.

8. The system of claim 1, wherein the three-dimensional surface is at least a segment of a cylindrical surface.

9. The system of claim 8, wherein the segment is a ring.

10. The system of claim 1, wherein the three-dimensional surface is an ellipsoid surface.

11. The system of claim 10, wherein the ellipsoid surface is at least a segment of a spherical surface.

12. The system of claim 1, wherein the tracker is a non-stereo tracker.

13. A method for tracking an item bearing at least one pattern tag, the pattern tag bearing a rotationally asymmetric pattern having a plurality of contrasting portions, at least one of the plurality of contrasting portions having a perimeter with a polygonal shape, the method comprising the steps of:
  obtaining from a tracker image information about the at least one pattern tag;
  obtaining from a database geometric information about the at least one pattern tag, the geometric information comprising a mathematical description of a polygonal perimeter of the at least one contrasting portion of the at least one pattern tag;
  determining within the image information a three-dimensional location of at least one pattern reference point of the at least one pattern tag based on the mathematical description of the polygonal perimeter, and
  determining within the image information a three-dimensional rotational orientation of the at least one pattern tag based on the geometric information.

14. The method of claim 13, wherein the plurality of contrasting portions has a predetermined random distribution; the geometric information includes predetermined distribution information about the random distribution; and the determining the three-dimensional location of the at least one pattern reference point comprises comparing the image information with the distribution information.

15. The method of claim 13, wherein the step of obtaining from a tracker image information involves obtaining non-stereo image information.

16. A surgical monitoring system comprising
  a tracker for obtaining image information of a surgical site;
  a fiducial reference configured for removably attaching to a location proximate the surgical site;
  a tracking marker in fixed three-dimensional spatial relationship with the fiducial reference and observable by the tracker, the tracking marker bearing at least one pattern comprising a plurality of contrasting portions and at least one of the contrasting portions having a perimeter with a polygonal shape, the tracking marker having a shape with a surface extending in three dimensions; and
  a controller configured to spatially relate image information to previously obtained scan data, the controller having a processor and a memory, the controller in communication with the tracker, the memory storing software that when executed by the processor determines the three-dimensional location and orientation of the fiducial reference by relating the image information to the scan data on the basis of the polygonal shape.

17. The system of claim 16, further including a display in communication with the controller, the controller further including software that when executed by the processor displays one of the position of the pattern tag in the image information from the tracker, potential trajectories of the pattern tag, and boundary conditions relating to the fiducial reference.

18. The system of claim 16, wherein the controller further includes software that when executed by the processor creates a model based on a previous scan and image information from the tracker, said system further comprising a display in communication with the controller and the controller includes further software that when executed by the controller displays the position of the pattern tag within the model on the display.

19. The system of claim 16, wherein the perimeter of the at least one contrasting portion is a square.

20. The system of claim 16, wherein the perimeter of the at least one contrasting portion is a triangle.

21. The system of claim 16, wherein the perimeter of the at least one contrasting portion is a hexagon.

22. The system of claim 16, wherein the three-dimensional surface is at least a segment of a cylindrical surface.

23. The system of claim 22, wherein the segment is ring.

24. The system of claim 22, wherein the three-dimensional surface is an ellipsoid surface.

25. The system of claim 24, wherein the ellipsoid surface is a segment of a spherical surface.

26. The system of claim 16, wherein the wherein the tracker is a non-stereo tracker.

27. A method for tracking an item bearing a pattern tag having at least one unique rotationally asymmetric pattern, the method comprising the steps of:
  obtaining image information from a tracker about the at least one pattern tag;
  identifying the at least one pattern tag within the image information on the basis of its unique pattern;
  obtaining from a database geometric information about the at least one pattern tag, the geometric information comprising a mathematical description of a polygonal perimeter of at least one contrasting portion of the at least one pattern tag;
  determining from the image information the location of at least one pattern reference point of the at least one pattern tag based on the mathematical description of the polygonal perimeter; and
  determining from the image information the three-dimensional rotational orientation of the at least one pattern tag based on the geometric information and the at least one pattern reference point.

28. The method of claim 27, wherein the step of obtaining image information from the tracker involves obtaining non-stereo image information from the tracker.

29. A method for tracking the location and rotational orientation of an item comprising the steps of:
- attaching to the item a tracking marker bearing a rotationally asymmetric pattern of contrasting portions, at least a section of the perimeter of at least one contrasting portion of the at least one pattern tag having a mathematical description;
- obtaining image information from a tracker about the at least one pattern tag;
- obtaining geometric information from a database about the at least one pattern tag, the geometric information comprising a mathematical description of a polygonal perimeter of at the least one contrasting portion of the at least one pattern tag;
- determining from the image information the three-dimensional location of at least one pattern reference point of the at least one pattern tag based on the geometric information; and
- determining within the image information the three-dimensional rotational orientation of the at least one pattern tag based on the mathematical description of the polygonal perimeter.

30. The method of claim 29, wherein the step of obtaining image information from a tracker involves obtaining non-stereo image information from the tracker.

31. The method of claim 29, wherein the plurality of contrasting portions have a predetermined random distribution; the geometric information includes predetermined distribution information about the random distribution; and the determining the three-dimensional location of the at least one pattern reference point comprises comparing the image information with the distribution information.

* * * * *